US012758195B2

(12) United States Patent
Jung

(10) Patent No.: US 12,758,195 B2
(45) Date of Patent: Oct. 13, 2026

(54) ULTRASONIC DIAGNOSTIC DEVICE AND CONTROL METHOD THEREOF

(71) Applicant: SAMSUNG MEDISON CO., LTD., Hongcheon-gun (KR)

(72) Inventor: Jaesun Jung, Hongcheon-gun (KR)

(73) Assignee: Samsung Medison Co., Ltd., Hongcheon-gun (KR)

( * ) Notice: Subject to any disclaimer, the term of this patent is extended or adjusted under 35 U.S.C. 154(b) by 35 days.

(21) Appl. No.: 18/895,935

(22) Filed: Sep. 25, 2024

(65) Prior Publication Data

US 2025/0143676 A1 May 8, 2025

(30) Foreign Application Priority Data

Nov. 2, 2023 (KR) ........................ 10-2023-0150331
Jul. 17, 2024 (KR) ........................ 10-2024-0094542

(51) Int. Cl.
*A61B 8/00* (2006.01)
*A61B 8/08* (2006.01)

(52) U.S. Cl.
CPC ................ *A61B 8/54* (2013.01); *A61B 8/085* (2013.01); *A61B 8/463* (2013.01)

(58) Field of Classification Search
CPC ........... A61B 8/54; A61B 8/085; A61B 8/463; A61B 8/4405; A61B 8/0866; A61B 8/5223; A61B 8/4427; A61B 8/465
See application file for complete search history.

(56) References Cited

U.S. PATENT DOCUMENTS

| | | | | |
|---|---|---|---|---|
| 2002/0042573 | A1 | 4/2002 | Hashimoto | |
| 2017/0086783 | A1 | 3/2017 | Denk | |
| 2017/0120080 | A1 * | 5/2017 | Phillips | A61B 34/25 |
| 2021/0219949 | A1 | 7/2021 | Qi | |
| 2022/0087644 | A1 | 3/2022 | Patil | |
| 2022/0344034 | A1 | 10/2022 | Roundhill | |

FOREIGN PATENT DOCUMENTS

| | | | |
|---|---|---|---|
| JP | 2016083192 | A | 5/2016 |
| KR | 20180100925 | A | 9/2018 |

* cited by examiner

*Primary Examiner* — Sanjay Cattungal
(74) *Attorney, Agent, or Firm* — Harvest IP Law, LLP

(57) ABSTRACT

Disclosed is a control method of an ultrasonic diagnostic device, which comprises a display configured to display an ultrasonic image corresponding to a scan area scanned by a probe, including identifying an object included in the scan area, determining a diagnostic subject based on at least one of the object or a user input received from an input interface, determining a scannable time for each object or diagnostic subject, and displaying an indicator for displaying the scannable time on the display.

18 Claims, 26 Drawing Sheets

D33

D42

ULTRASONIC DIAGNOSTIC DEVICE AND CONTROL METHOD THEREOF

CROSS-REFERENCE TO RELATED APPLICATION(S)

This application is based on and claims priority under 35 U.S.C. § 119 to Korean Patent Application Nos. 10-2023-0150331 and 10-2024-0094542, filed on Nov. 2, 2023 and Jul. 17, 2024, in the Korean Intellectual Property Office, the disclosure of which is incorporated by reference herein in its entirety.

BACKGROUND

1. Field

The disclosure relates to an ultrasonic diagnostic device for obtaining ultrasonic images and a control method thereof.

2. Description of the Related Art

Recently, in a medical field, various medical imaging devices have been widely used to image and obtain information about biological tissues of a human body for the purpose of early diagnosis of various diseases or surgery. Representative examples of such medical imaging devices may include ultrasonic diagnostic devices, CT devices, and MRI devices.

An ultrasonic imaging device is a device that emits an ultrasonic signal generated from a transducer of a probe to an object, and non-invasively obtains at least one image of a region inside the object (e.g., soft tissue or blood flow) by receiving information from the signal reflected from the object. In particular, an ultrasonic diagnostic device is used for medical purposes such as observing the inside of an object, detecting foreign substances, and measuring injury. Such an ultrasonic diagnostic device is widely used together with other imaging diagnostic devices because the ultrasonic imaging device has higher stability than a diagnostic device using an X-ray, may display images in real time, and is safe because there is no radiation exposure.

In order to use ultrasonic diagnostic devices safely, it is required to use the ultrasound diagnostic devices while maintaining the ALARA (as-low-as-reasonably-achievable) principle, that is, 'maintaining the lowest level reasonably achievable'.

Therefore, conventional ultrasonic diagnostic devices provide various UIs so that users may adhere to the ALARA principle, and as an example, a mechanical index (MI) indicating a mechanical effect applied to an object or a thermal index (TI) indicating the possibility of a temperature increase due to irradiation of an ultrasound beam to an object is displayed on a display device. However, a UI providing information about the scan time, which is one of the most important factors in adhering to the ALARA (as-low-as-reasonably-achievable) principle, is not displayed, which may cause a problem of not properly guiding the user.

SUMMARY

It is an aspect of the disclosure to provide an ultrasonic diagnostic device and a control method thereof capable of preventing an object from being exposed to ultrasound for a long time by displaying a cumulative scan time so that a user may adhere to the ALARA principle.

Additional aspects of the disclosure will be set forth in part in the description which follows and, in part, will be obvious from the description, or may be learned by practice of the disclosure.

In accordance with an aspect of the disclosure, a control method of an ultrasonic diagnostic device, which includes a display configured to display an ultrasonic image corresponding to a scan area scanned by a probe, includes identifying an object included in the scan area, determining a diagnostic subject based on a user input received from the object or an input interface, determining a scannable time for each object or diagnostic subject, and displaying an indicator for displaying the scannable time on the display.

In accordance with another aspect of the disclosure, an ultrasonic diagnostic device includes a display configured to display an ultrasonic image, an input interface configured to receive a user input for controlling display of the ultrasonic image, and a processor configured to identify an object included in a scan area, determine a diagnostic subject based on the user input received from the object or the input interface, determine a scannable time for each object or diagnostic subject, and control the display to display an indicator for displaying the scannable time.

BRIEF DESCRIPTION OF THE DRAWINGS

These and/or other aspects of the disclosure will become apparent and more readily appreciated from the following description of the embodiments, taken in conjunction with the accompanying drawings of which.

DETAILED DESCRIPTION

Figure 1:
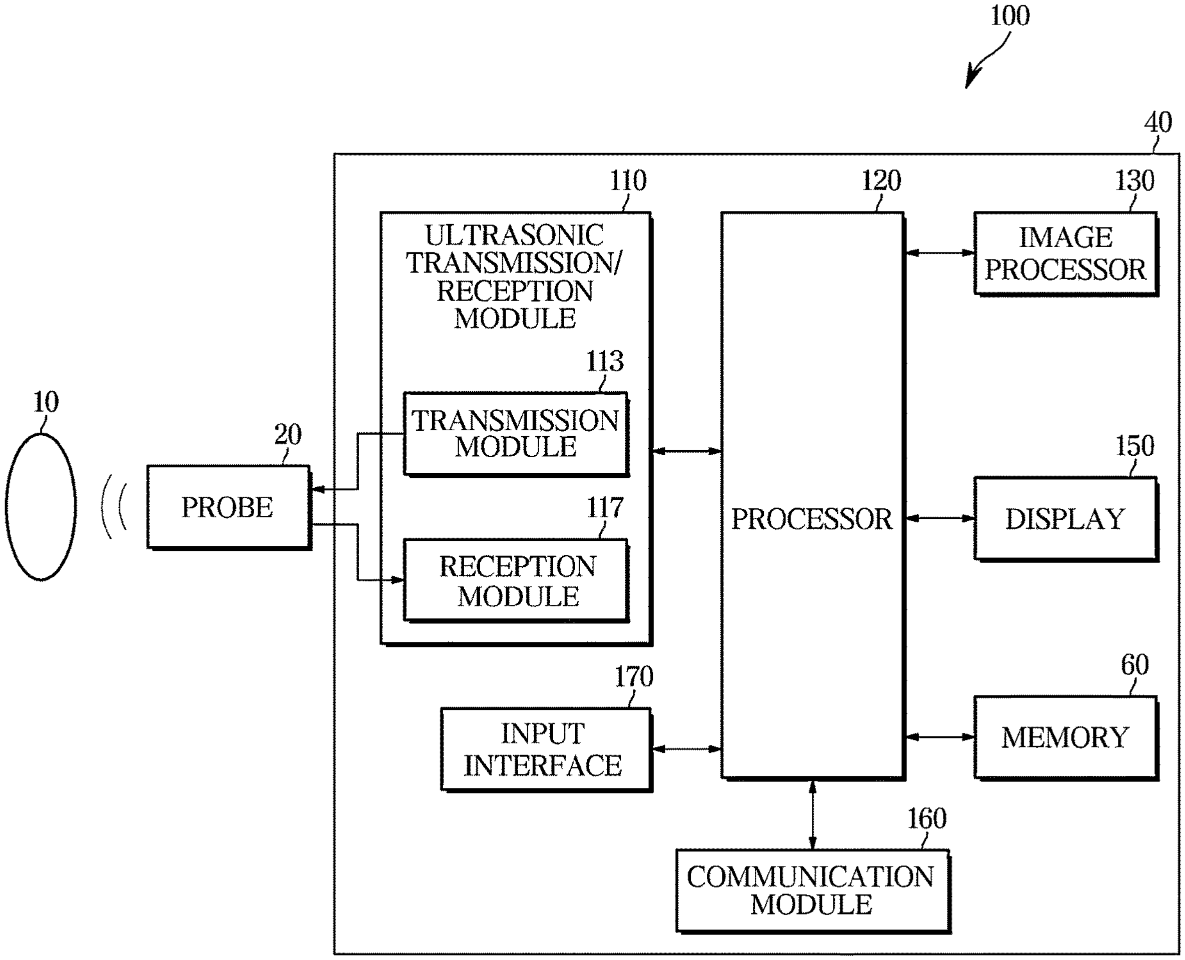
FIG. 1 illustrates a control block diagram of an ultrasonic imaging system 100 in a case in which a probe 20 is a wired probe or a hybrid probe.

This disclosure will explain the principles and disclose embodiments of the disclosure to clarify the scope of the claims of the disclosure and enable those skilled in the art to which the embodiments of the disclosure belong to practice the embodiments. The embodiments of the disclosure may be implemented in various forms.

Throughout the specification, like reference numbers refer to like elements throughout this specification. This specification does not describe all components of the embodiments, and general contents in the technical field to which the disclosure belongs or overlapping contents between the embodiments will not be described. The "module" or "unit" used in the specification may be implemented as one or a combination of two or more of software, hardware, or firmware, and according to embodiments, a plurality of "module" or "unit" may be implemented as a single element, or a single "module" or "unit" may include a plurality of elements.

The singular form of a noun corresponding to an item may include a single item or a plurality of items, unless the relevant context clearly indicates otherwise.

In this disclosure, each of phrases such as "A or B," "at least one of A and B," "at least one of A or B," "A, B or C," "at least one of A, B and C," and "at least one of A, B, or C" may include any one of the items listed together in the corresponding one of the phrases, or all possible combinations thereof.

The term "and/or" includes any combination of a plurality of related components or any one of a plurality of related components.

The terms such as "first," "second," "primary," and "secondary" may simply be used to distinguish a given component from other corresponding components, and do not limit the corresponding components in any other respect (e.g., importance or order).

The terms "front surface," "rear surface," "upper surface," "lower surface," "side surface," "left side," "right side," "upper portion," "lower portion," and the like used in the disclosure are defined with reference to the drawings, and the shape and position of each component are not limited by these terms.

The terms "comprises," "has," and the like are intended to indicate that there are features, numbers, steps, operations, components, parts, or combinations thereof described in the disclosure, and do not exclude the presence or addition of one or more other features, numbers, steps, operations, components, parts, or combinations thereof.

When any component is referred to as being "connected," "coupled," "supported," or "in contact" with another component, this includes a case in which the components are indirectly connected, coupled, supported, or in contact with each other through a third component as well as directly connected, coupled, supported, or in contact with each other.

When any component is referred to as being located "on" or "over" another component, this includes not only a case in which any component is in contact with another component but also a case in which another component is present between the two components.

Hereinafter, an ultrasonic device according to various embodiments will be described in detail with reference to the accompanying drawings. When described with reference to the attached drawings, similar reference numbers may be assigned to identical or corresponding components and redundant description thereof may be omitted.

In this disclosure, images may include a medical image obtained by a medical imaging device, such as a magnetic resonance imaging (MRI) device, a computed tomography (CT) device, an ultrasonic imaging device, and an x-ray imaging device.

In this disclosure, an 'object', which is subject to photography, may include a person, animal, or part thereof. For example, the object may include a part of a human body (organ, etc.) or a phantom.

Throughout this disclosure, an 'ultrasonic image' refers to an image of an object that has been processed based on an ultrasonic signal transmitted to and reflected from the object.

Hereinafter, embodiments will be described in detail with reference to the drawings.

Figure 2:
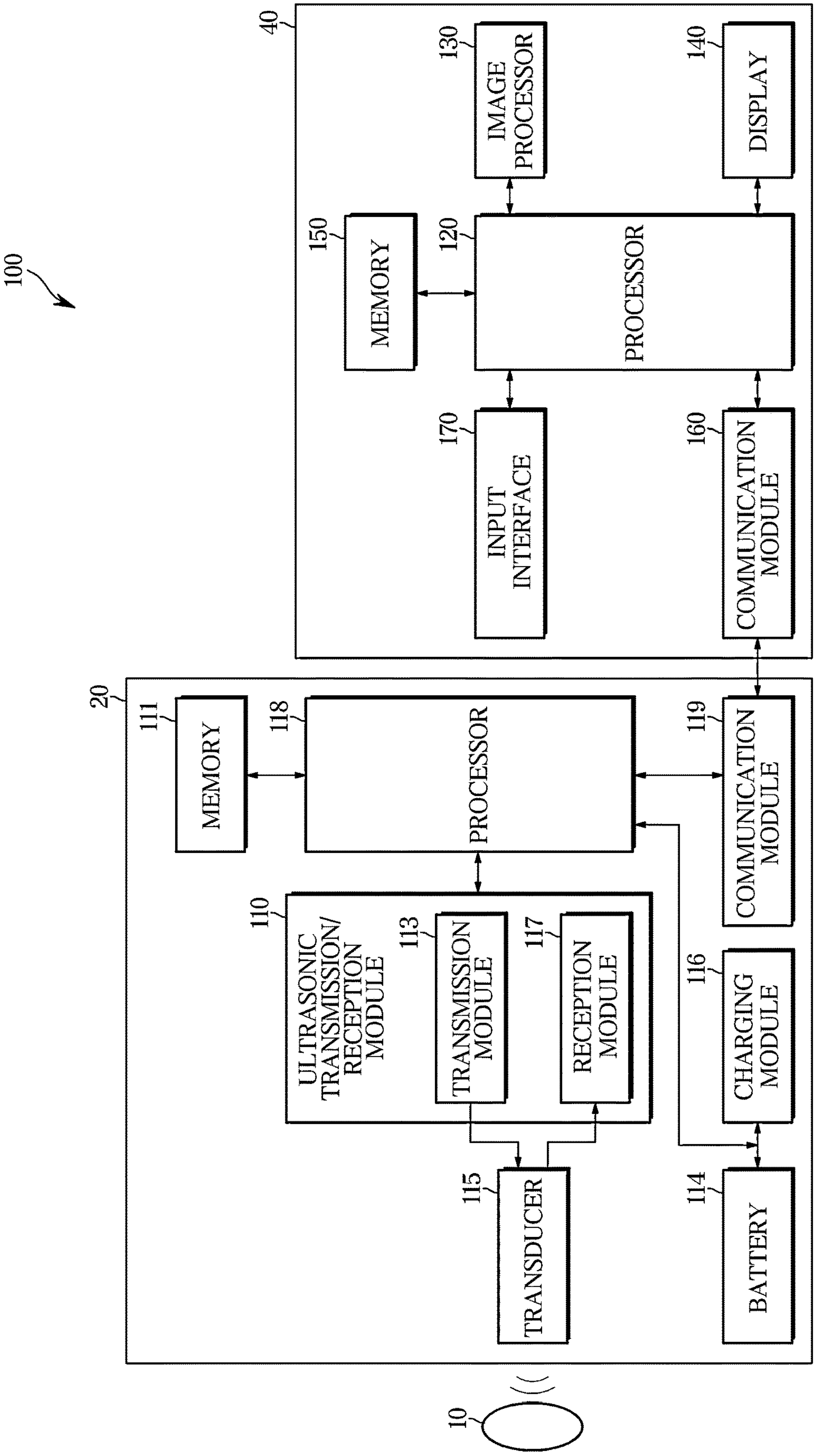
FIG. 2 illustrates a control block diagram of the ultrasonic imaging system 100 in a case in which the probe 20 is a wireless probe or a hybrid probe.

Referring to FIGS. 1 and 2, an ultrasonic imaging system 100 may include a probe 20 and an ultrasonic diagnostic device 40.

The ultrasonic diagnostic device 40 may be implemented not only in a cart type but also in a portable type. A portable ultrasonic imaging device may include, for example, a smart phone, laptop computer, PDA, tablet PC, etc., which include a probe and an application, but is not limited thereto.

The probe 20 may include a wired probe connected to the ultrasonic diagnostic device 40 by wire to communicate with the ultrasonic diagnostic device 40 by wire, a wireless probe wirelessly connected to the ultrasonic diagnostic device 40 to communicate wirelessly with the ultrasonic diagnostic device 40, and/or a hybrid probe by wire or wirelessly connected to the ultrasonic diagnostic device 40 to communicate by wire or wirelessly with the ultrasonic diagnostic device 40.

According to various embodiments, as illustrated in FIG. 1, the ultrasonic diagnostic device 40 may include an ultrasonic transmission/reception module 110, or as illustrated in FIG. 2, the probe 20 may include the ultrasonic transmission/reception module 110. According to various embodiments, both the ultrasonic diagnostic device 40 and the probe 20 may also include the ultrasonic transmission/reception module 110.

According to various embodiments, the probe 20 may further include an image processor 130, a display 140, and/or an input interface 170.

Accordingly, the descriptions of the ultrasonic transmission/reception module 110, the image processor 130, the display 140, and/or the input interface 170 included in the ultrasonic diagnostic device 40 may also be applied to the ultrasonic transmission/reception module 110, the image processor 130, the display 140, and/or the input interface 170 included in the probe 20.

FIG. 1 illustrates a control block diagram of the ultrasonic imaging system 100 in a case in which the probe 20 is a wired probe or a hybrid probe.

The probe 20 may include a plurality of transducers. The plurality of transducers may transmit an ultrasonic signal to an object 10 in response to a transmission signal applied from a transmission module 113. The plurality of transducers may form a received signal by receiving the ultrasonic signal (echo signal) reflected from the object 10. The probe 20 may be implemented as an integrated type with the ultrasonic diagnostic device 40, or may be implemented as a separate type connected to the ultrasonic diagnostic device 40 by wire. The ultrasonic diagnostic device 40 may be connected to the one or more probes 20 depending on the implementation type.

In a case in which the probe 20 is a wired probe or a hybrid probe, the probe 20 may include a cable and a connector capable of being connected to a connector of the ultrasonic diagnostic device 40.

The probe 20 according to an embodiment may be implemented as a two-dimensional probe. In a case in which the probe 20 is implemented as a two-dimensional probe, the plurality of transducers included in the probe 20 may be arranged in two dimensions to form a two-dimensional transducer array.

For example, the two-dimensional transducer array may have a form in which a plurality of sub-arrays including the plurality of transducers arranged in a first direction is arranged in a second direction different from the first direction.

In addition, in the case in which the probe 20 according to an embodiment is implemented as a two-dimensional probe, the ultrasonic transmission/reception module 110 may include an analog beamformer and a digital beamformer. Alternatively, the two-dimensional probe may include one or both of the analog beamformer and the digital beamformer depending on the implementation type.

A processor 120 controls the transmission module 113 to form a transmission signal to be applied to each of the transducers 115 in consideration of positions and focused points of the plurality of transducers included in the probe 20.

The processor 120 may control a reception module 117 to generate ultrasonic data by converting reception signals received from the probe 20 to analog to digital and summing up the digitally converted reception signals in consideration of the positions and focused points of the plurality of transducers.

In the case in which the probe 20 is implemented as a two-dimensional probe, the processor 120 may calculate a time delay value for digital beamforming for each sub-array for each of the plurality of sub-arrays included in the two-dimensional transducer array. The processor 120 may also calculate a time delay value for analog beamforming for each of the transducers included in one of the plurality of sub-arrays. The processor 120 may control the analog beamformer and the digital beamformer to form a transmission signal to be applied to each of the plurality of transducers depending on the time delay values for analog beamforming and the time delay values for digital beamforming. The processor 120 may also control the analog beamformer to sum up the signals received from the plurality of transducers for each sub-array depending on the time delay values for analog beamforming. The processor 120 may also control the ultrasonic transmission/reception module 110 to convert the summed signal for each sub-array to analog to digital. The processor 120 may also control the digital beamformer to generate ultrasonic data by summing up the digitally converted signals depending on the time delay values for digital beamforming.

The image processor 130 generates an ultrasonic image using the generated ultrasonic data.

The display 140 may display the generated ultrasonic image and a variety of information processed by the ultrasonic diagnostic device 40 and/or the probe 20. The probe 20 and/or the ultrasonic diagnostic device 40 may include the one or more displays 140 depending on the implementation type. The display 140 may also include a touch panel or a touch screen.

The display 140 may output four-dimensional ultrasonic images according to control commands of the processor 120. The four-dimensional ultrasonic image may mean providing three-dimensional images in real time by adding the dimension of time. For example, the four-dimensional ultrasonic image may be an ultrasonic image that includes fetal movements, heartbeats, or other motions of a biological tissue over time. The four-dimensional ultrasonic image may be implemented based on ultrasonic image data obtained in real time or ultrasonic image data previously stored in a memory 150.

The processor 120 may control the overall operation of the ultrasonic diagnostic device 40 and signal flows between internal components of the ultrasonic diagnostic device 40. The processor 120 may perform or control various operations or functions of the ultrasonic diagnostic device 40 by executing programs or instructions stored in the memory 150. The processor 120 may also control an operation of the ultrasonic diagnostic device 40 by receiving a control signal from the input interface 170 or an external device.

The ultrasonic diagnostic device 40 may include a communication module 160, and may be connected to an external device (e.g., the probe 20, a server, medical device, portable device (a smart phone, tablet PC, wearable device, etc.)) through the communication module 160.

The communication module 160 may include one or more components that enable communication with the external device, and may include, for example, at least one of a short-range communication module, a wired communication module, and a wireless communication module.

The communication module 160 may receive a control signal and data from the external device, and may transmit the received control signal to the processor 120 to enable the processor 120 to control the ultrasonic diagnostic device 40 depending on the received control signal.

Alternatively, the processor 120 may transmit a control signal to an external device through the communication module 160 to control the external device depending on the control signal of the processor.

For example, the external device may process data in the external device depending on the control signal of the processor received through the communication module.

A program capable of controlling the ultrasonic diagnostic device 40 may be installed in the external device, and this program may include instructions for performing some or all of the operations of the processor 120.

The program may be pre-installed on the external device, or a user of the external device may download and install the program from a server providing an application. The server providing the application may include a recording medium in which the program is stored.

The memory 150 may store various data or programs for driving and controlling the ultrasonic diagnostic device 40, inputted and outputted ultrasonic data, ultrasonic images, etc.

The input interface 170 may receive a user input for controlling the ultrasonic diagnostic device 40. For example, the user input may include, but is not limited to, input of manipulating a button, a keypad, a mouse, a trackball, a jog switch, a knob, and the like, input of touching a touch pad or touch screen, voice input, motion input, biometric information input (e.g., iris recognition, fingerprint recognition, etc.), and the like.

FIG. 2 illustrates a control block diagram of the ultrasonic imaging system 100 in a case in which the probe 20 is a wireless probe or a hybrid probe.

According to various embodiments, the ultrasonic diagnostic device 40 illustrated in FIG. 2 may be replaced with the ultrasonic diagnostic device 40 described with reference to FIG. 1.

According to various embodiments, the probe 20 illustrated in FIG. 1 may be replaced with the probe 20 to be described with reference to FIG. 2.

The probe 20 may include the transmission module 113, a battery 114, the transducer 115, a charging module 116, the reception module 117, a processor 118, and a communication module 119. Although FIG. 1 illustrates that the probe 20 includes both the transmission module 113 and the reception module 117, the probe 20 may include only part of a configuration of the transmission module 113 and the reception module 117 depending on the implementation type, and the part of the configuration of the transmission module 113 and the reception module 117 may be included in the ultrasonic diagnostic device 40. Alternatively, the probe 20 may further include the image processor 130.

The transducer 115 may include a plurality of transducers. The plurality of transducers may transmit an ultrasonic signal to the object 10 in response to a transmission signal applied from the transmission module 113. The plurality of transducers may receive the ultrasonic signal reflected from the object 10 to form a reception signal.

The charging module 116 may charge the battery 114. The charging module 116 may receive electric power from the outside. The charging module 116 may receive electric power wirelessly. However, the disclosure is not limited thereto, and the charging module 116 may receive electric power by wire. The charging module 116 may transfer the received electric power to the battery 114.

The processor 118 controls the transmission module 113 to form a transmission signal to be applied to each of the plurality of transducers in consideration of the positions and focused points of the plurality of transducers.

The processor 118 controls the reception module 117 to generate ultrasonic data by converting reception signals received from the transducer 115 to analog to digital and summing up the digitally converted reception signals in consideration of the positions and focused points of the plurality of transducers. Alternatively, in a case in which the probe 20 includes the image processor 130, the probe 20 may generate an ultrasonic image using the generated ultrasonic data.

In the case in which the probe 20 is implemented as a two-dimensional probe, the processor 118 may calculate a time delay value for digital beamforming for each sub-array for each of the plurality of sub-arrays included in the two-dimensional transducer array. The processor 118 may also calculate a time delay value for analog beamforming for each of the transducers included in one of the plurality of sub-arrays. The processor 118 may control the analog beamformer and the digital beamformer to form a transmission signal to be applied to each of the plurality of transducers depending on the time delay values for analog beamforming and the time delay values for digital beamforming. The processor 118 may also control the analog beamformer to sum up the signals received from the plurality of transducers for each sub-array depending on the time delay values for analog beamforming. The processor 118 may also control the ultrasonic transmission/reception module 110 to convert the summed signal for each sub-array to analog to digital. The processor 118 may also control the digital beamformer to generate ultrasonic data by summing up the digitally converted signals depending on the time delay values for digital beamforming.

The processor 118 may control the overall operation of the probe 20 and the signal flows between the internal components of the probe 20. The processor 118 may perform or control the various operations or functions of the probe 20 by executing programs or instructions stored in a memory 111. The processor 118 may also control the operation of the probe 20 by receiving a control signal from the input interface 170 of the probe 20 or an external device (e.g., the ultrasonic diagnostic device 40).

The communication module 119 may wirelessly transmit the generated ultrasonic data or ultrasonic images to the ultrasonic diagnostic device 40 through a wireless network. The communication module 119 may also receive a control signal and data from the ultrasonic diagnostic device 40.

The ultrasonic diagnostic device 40 may receive the ultrasonic data or ultrasonic images from the probe 20.

In an embodiment, in the case in which the probe 20 includes the image processor 130 capable of generating ultrasonic images using the ultrasonic data, the probe 20 may transmit the ultrasonic data and/or the ultrasonic images generated by the image processor 130 to the ultrasonic diagnostic device 40.

In an embodiment, in a case in which the probe 20 does not include the image processor 130 capable of generating ultrasonic images using the ultrasonic data, the probe 20 may transmit the ultrasonic data to the ultrasonic diagnostic device 40. The ultrasonic data may include ultrasonic raw data, and the ultrasonic images may refer to ultrasonic image data.

The ultrasonic diagnostic device 40 may include the processor 120, the image processor 130, the display 140, the memory 150, the communication module 160, and the input interface 170.

The image processor 130 generates ultrasonic images using the ultrasonic data received from the probe 20.

The display 140 may display the ultrasonic images received from the probe 20, ultrasonic images generated by processing the ultrasonic data received from the probe 20, and a variety of information processed by the ultrasonic imaging system 100. The ultrasonic diagnostic device 40 may include the one or more displays 140 depending on the implementation type. The display 140 may also include a touch panel or a touch screen.

The processor 120 may control the overall operation of the ultrasonic diagnostic device 40 and the signal flows between the internal components of the ultrasonic diagnostic device 40. The processor 120 may perform or control the various operations or functions of the ultrasonic diagnostic device 40 by executing the programs or applications stored in the memory 150. The processor 120 may also control the operation of the ultrasonic diagnostic device 40 by receiving a control signal from the input interface 170 or an external device.

The ultrasonic diagnostic device 40 may include the communication module 160, and may be connected to an external device (e.g., the probe 20, a server, medical device, portable device (a smart phone, tablet PC, wearable device, etc.)) through the communication module 160.

The communication module 160 may include one or more components that enable communication with the external device, and may include, for example, at least one of the short-range communication module, the wired communication module, and the wireless communication module.

The communication module 160 of the ultrasonic diagnostic device 40 and the communication module 119 of the probe 20 may communicate using a network or a short-range wireless communication method. For example, the communication module 160 of the ultrasonic diagnostic device 40 and the communication module 119 of the probe 20 may communicate using any one of wireless LAN, Wi-Fi, Bluetooth, ZigBee, Wi-Fi Direct (WFD), Infrared Data Association (IrDA), Bluetooth Low Energy (BLE), Near Field Communication (NFC), Wireless Broadband Internet (WiBro), World Interoperability for Microwave Access (WIMAX), Shared Wireless Access Protocol (SWAP), Wireless Gigabit Alliance (WiGig), RF communication, a wireless data communication method including 60 GHz millimeter wave (mm wave) short-range communication, etc.

To this end, the communication module 160 of the ultrasonic diagnostic device 40 and the communication module 119 of the probe 20 may include at least one of a wireless LAN communication module, a Wi-Fi communication module, a Bluetooth communication module, a ZigBee communication module, a Wi-Fi Direct (WFD) communication module, an Infrared Data Association (IrDA) communication module, a Bluetooth Low Energy (BLE) communication module, a Near Field Communication (NFC) module, a Wireless Broadband Internet (WiBro) communication module, a World Interoperability for Microwave Access (WiMAX) communication module, a Shared Wireless Access Protocol (SWAP) communication module, a Wireless Gigabit Alliance (WiGig) communication module, a RF communication module, and a 60 GHz millimeter wave (mm wave) short-range communication module.

In an embodiment, the probe 20 may transmit device information (e.g., ID information) of the probe 20 using a first communication method (e.g., BLE), may be wirelessly paired with the ultrasonic diagnostic device 40, and may transmit ultrasonic data and/or ultrasonic images to the paired ultrasonic diagnostic device 40.

The device information of the probe 20 may include a variety of information related to a serial number, model name, and battery state of the probe 20.

The ultrasonic diagnostic device 40 may receive the device information (e.g., ID information) of the probe 20 from the probe 20 using the first communication method (e.g., BLE), may be wirelessly paired with the probe 20, may transmit an activation signal to the paired probe 20, and may receive the ultrasonic data and/or ultrasonic images from the probe 20. In this case, the activation signal may include a signal for controlling the operation of the probe 20.

In an embodiment, the probe 20 may transmit the device information (e.g., ID information) of the probe 20 using the first communication method (e.g., BLE), may be wirelessly paired with the ultrasonic diagnostic device 40, and may transmit the ultrasonic data and/or ultrasonic images to the ultrasonic diagnostic device 40 paired by the first communication method using a second communication method (e.g., 60 GHz millimeter wave and Wi-Fi).

The ultrasonic diagnostic device 40 may receive the device information (e.g., ID information) of the probe 20 from the probe 20 using the first communication method (e.g., BLE), may be wirelessly paired with the probe 20, may transmit the activation signal to the paired probe 20, and may receive the ultrasonic data and/or ultrasonic images from the probe 20 using the second communication method (e.g., 60 GHz millimeter wave and Wi-Fi).

According to various embodiments, the first communication method used to pair the probe 20 and the ultrasonic diagnostic device 40 with each other may have a lower frequency band than a frequency band of the second communication method used by the probe 20 to transmit the ultrasonic data and/or ultrasonic images to the ultrasonic diagnostic device 40.

The display 140 of the ultrasonic diagnostic device 40 may display UIs indicating the device information of the probe 20. For example, the display 140 may display UIs, which indicate identification information of the wireless probe 20, a pairing method indicating a pairing method with the probe 20, a data communication state between the probe 20 and the ultrasonic diagnostic device 40, a method of performing data communication with the ultrasonic diagnostic device 40, and the battery state of the probe 20.

In a case in which the probe 20 includes the display 140, the display 140 of the probe 20 may display UIs indicating the device information of the probe 20. For example, the display 140 may display UIs, which indicate the identification information of the wireless probe 20, the pairing method indicating the pairing method with the probe 20, the data communication state between the probe 20 and the ultrasonic diagnostic device 40, the method of performing data communication with the ultrasonic diagnostic device 40, and the battery state of the probe 20.

The communication module 160 may also receive a control signal and data from an external device and transmit the received control signal to the processor 120 so that the processor 120 controls the ultrasonic diagnostic device 40 depending on the received control signal.

Alternatively, the processor 120 may transmit a control signal to an external device through the communication module 160 to control the external device depending on the control signal of the processor 120.

For example, the external device may process data of the external device depending on the control signal of the processor 120 received through the communication module.

A program capable of controlling the ultrasonic diagnostic device 40 may be installed in the external device, and this program may include instructions for performing some or all of the operations of the processor 120.

The program may be pre-installed on the external device, or a user of the external device may download and install the program from a server providing the application. The server providing the application may include the recording medium in which the program is stored.

The memory 150 may store various data or programs for driving and controlling the ultrasonic diagnostic device 40, inputted and outputted ultrasonic data, ultrasonic images, etc.

Examples of the ultrasonic imaging system 100 according to an embodiment of the disclosure will be described later through FIGS. 3, 4, 5, and 6.

FIGS. 3, 4, 5, and 6 are views illustrating ultrasonic imaging devices according to an embodiment.

Figure 3:
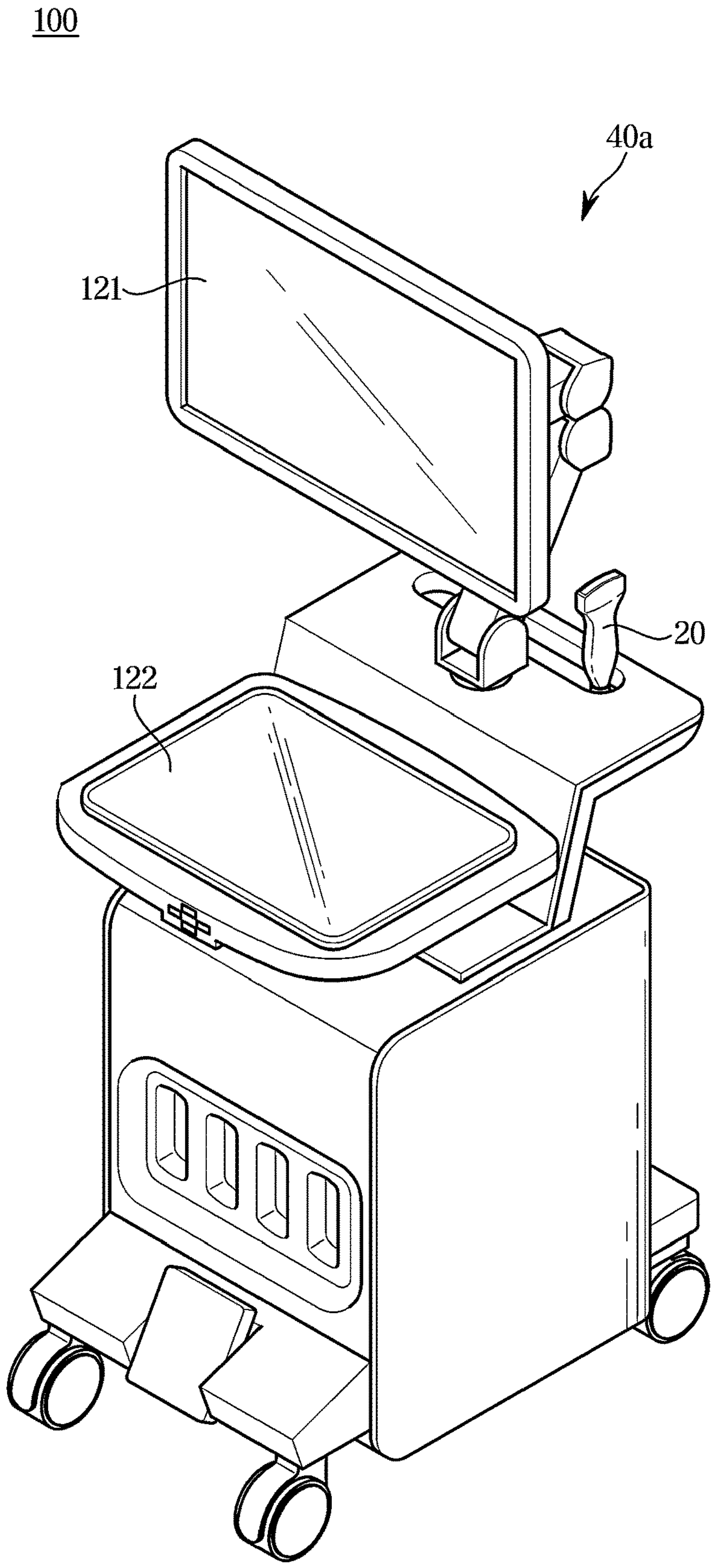
FIGS. 3 to 6 are views illustrating the ultrasonic imaging system 100 according to an embodiment.
Figure 4:
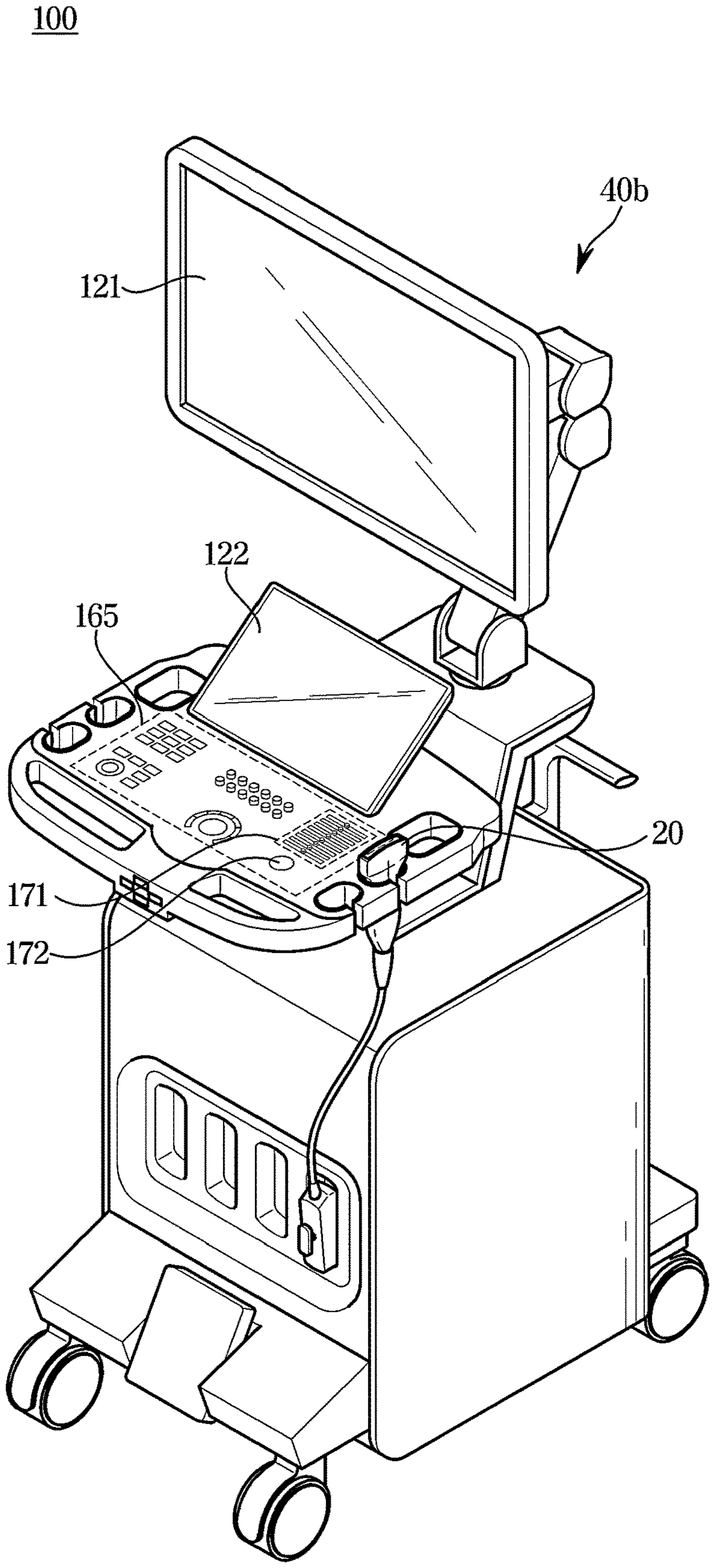

Referring to FIGS. 3 and 4, ultrasonic imaging devices 40*a* and 40*b* may include a main display 121 (140) and a sub display 122 (140). At least one of the main display 121 and the sub display 122 may be implemented as a touch screen. At least one of the main display 121 and the sub display 122 may display ultrasonic images or a variety of information processed by the ultrasonic imaging devices 40*a* and 40*b*. In addition, at least one of the main display 121 and the sub display 122 may be implemented as a touch screen and provide GUIs, so that data for controlling the ultrasonic imaging devices 40*a* and 40*b* may be inputted from the user. For example, the main display 121 may display ultrasonic images, and the sub display 122 may display a control panel (e.g., control panel 165 in FIG. 4) for controlling the display of the ultrasonic images in the form of GUIs. The sub display 122 may be provided with data for controlling the display of images through the control panel displayed in the form of GUIs. For example, a time gain compensation (TGC) button, a Freeze button, a trackball, a jog switch, a knob, and the like may be provided as GUIs on the sub display 122.

The ultrasonic imaging devices 40*a* and 40*b* may control the display of ultrasonic images displayed on the main display 121 using the inputted control data. The ultrasonic imaging devices 40*a* and 40*b* may also be connected to the probe 20 by wire or wirelessly to transmit and receive ultrasonic signals to and from the object.

Referring to FIG. 4, the ultrasonic imaging device 40*b* may further include a control panel 165 in addition to the main display 121 and the sub display 122. The control panel 165 may include a button, a trackball, a jog switch, a knob, and the like, and may be provided with data for controlling the ultrasonic imaging device 40*b* from the user. For example, the control panel 165 may include a time gain compensation (TGC) button 171, a Freeze button 172, and the like. The TGC button 171 is a button for setting a TGC value for each depth of the ultrasonic images. When the input of the Freeze button 172 is sensed while scanning an ultrasonic image, the ultrasonic imaging device 40*b* may maintain a state in which the frame image at that point in time is displayed.

A button, a trackball, a jog switch, a knob, and the like included in the control panel 165 may be provided as GUIs on the main display 121 or the sub display 122. The ultrasonic imaging devices 40*a* and 40*b* may be connected to the probe 20 to transmit and receive ultrasonic signals to and from the object 10.

Figure 5:
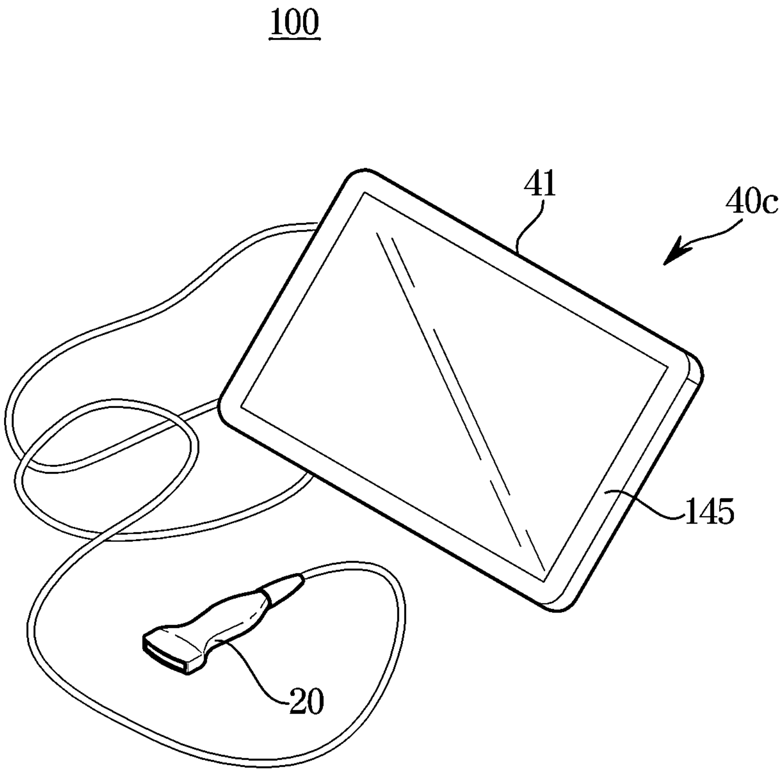
Figure 6:
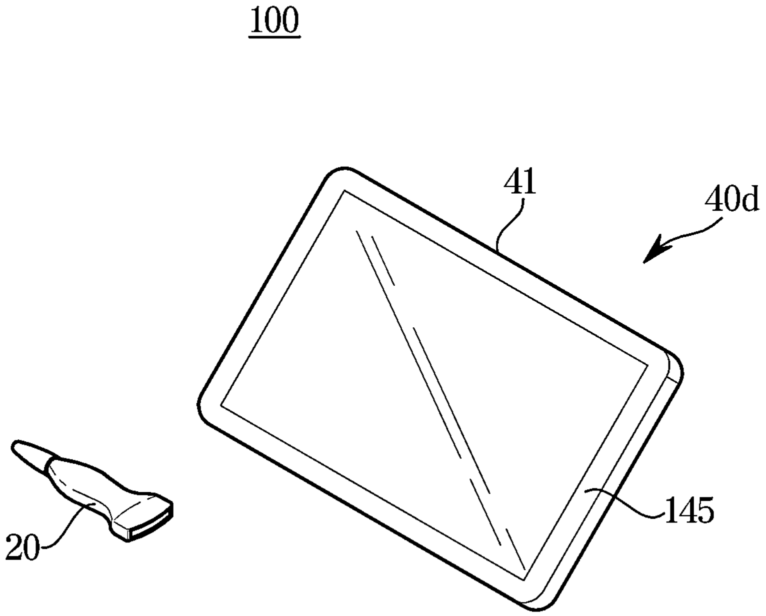

Referring to FIGS. 5 and 6, an ultrasonic diagnostic device 40*c* may also be implemented in a portable type. The portable ultrasonic imaging device 40*c* may include, for example, a smart phone, laptop computer, PDA, tablet PC, etc., which include a probe and an application, but is not limited thereto.

The ultrasonic imaging device 40*c* may include a main body 41. Referring to FIG. 5, the probe 20 may be connected to one side of the main body 41 by wire. To this end, the main body 41 may include a connection terminal to and from which a cable connected to the probe 20 may be attached and detached, and the probe 20 may include a connection terminal to and from which a cable connected to the main body 41 may be attached and detached.

Referring to FIG. 6, the probe 20 may be wirelessly connected to the ultrasonic diagnostic device 40. The main body 41 may include an input/output interface (e.g., a touch screen) 145 (140 and 170). Ultrasonic images, a variety of information processed by the ultrasonic imaging device, GUIs, and the like may be displayed on the input/output interface 145.

An ultrasonic image may be displayed on the input/output interface 145. The ultrasonic imaging device 40*c* may correct the ultrasonic image displayed on the input/output interface 145 using AI. The ultrasonic imaging device 40*c* may provide an alarm for informing using various audio-visual tools, such as graphics, sound, and vibration, information about lesions among the ultrasonic images displayed on the input/output interface 145 using AI.

The ultrasonic imaging device 40*c* may output a control panel displayed in the form of GUIs through the input/output interface 145.

An ultrasonic imaging device 40*d* and the probe 20 may establish communication or be paired using a short-range wireless communication. For example, the ultrasonic imaging device 40*d* and the probe 20 may perform communication using Bluetooth, BLE, Wi-Fi, or Wi-Fi Direct.

The ultrasonic imaging devices 40*c* and 40*d* may execute a program or application related to the probe 20 to control the probe 20 and output information related to the probe 20. The ultrasonic imaging devices 40*c* and 40*d* may perform operations related to the probe 20 while communicating with a predetermined server. The probe 20 may be registered with the ultrasonic imaging devices 40*c* and 40*d* or may be registered with the predetermined server. The ultrasonic imaging devices 40*c* and 40*d* may communicate with the registered probe 20 and perform the operations related to the probe 20.

The ultrasonic imaging devices 40*c* and 40*d* may include various types of input/output interfaces such as speakers, LEDs, and vibration devices. For example, the ultrasonic imaging devices 40*c* and 40*d* may output a variety of information in the form of graphics, sound, or vibration through the input/output interface. The ultrasonic imaging devices 40*c* and 40*d* may also output various notifications or data through the input/output interface.

According to an embodiment of the disclosure, the ultrasonic imaging device 40*a*, 40*b*, 40*c*, or 40*d* may process ultrasonic images or obtain additional information from ultrasonic images, using an artificial intelligence (AI) model. According to an embodiment of the disclosure, the ultrasonic imaging device 40*a*, 40*b*, 40*c*, or 40*d* may generate an ultrasonic image or perform processing such as correction, image quality improvement, encoding, and decoding on the ultrasonic image, using the AI model. In addition, according to an embodiment of the disclosure, the ultrasonic imaging device 40*a*, 40*b*, 40*c*, or 40*d* may perform processing, such as baseline definition, anatomical information acquisition, lesion information acquisition, surface extraction, boundary definition, length measurement, area measurement, volume measurement, and annotation creation, from ultrasonic images using the AI model.

The AI model may be provided on the ultrasonic imaging device 40*a*, 40*b*, 40*c*, or 40*d*, or may be provided on a server.

The AI model may be implemented using various artificial neural network models or deep neural network models. In addition, the AI model may be learned and created using various machine learning algorithms or deep learning algorithms. The AI model may be implemented using, for example, a model such as a convolutional neural network (CNN), a recurrent neural network (RNN), a generative adversarial network (GAN), and a long short-term memory (LSTM).

Figure 7:
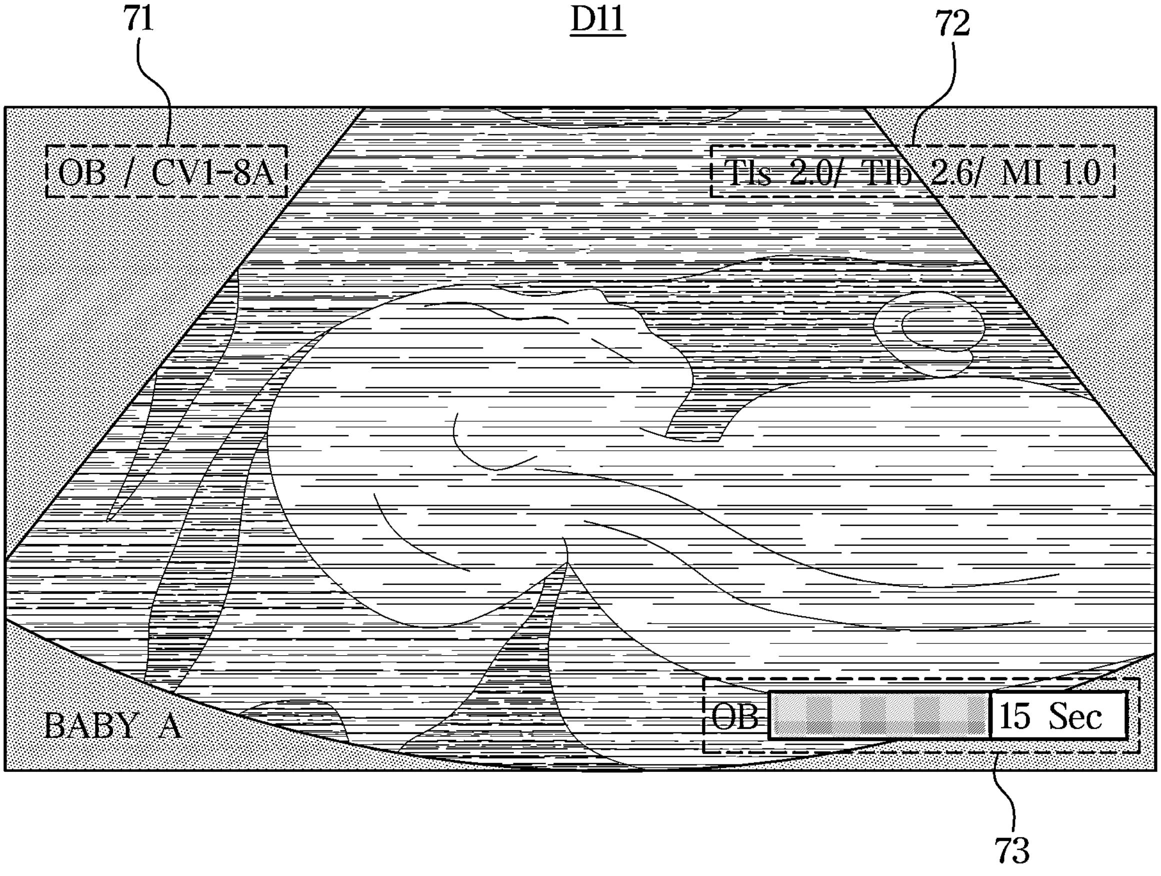
FIG. 7 is a diagram illustrating a screen D11 and a plurality of indicators displayed on a display of an ultrasonic imaging device according to an embodiment.

FIG. 7 is a diagram illustrating a screen D11 and a plurality of indicators displayed on a display of an ultrasonic imaging device according to an embodiment.

According to an embodiment, the display 140 of the ultrasonic diagnostic device 40 (e.g., the main display 121 or the sub display 122 in FIGS. 3 and 4) may display at least one of indicators 71, 72, and 73 for displaying an ultrasonic image or variety of information processed by the ultrasonic diagnostic device 40.

In this case, the at least one of the indicators 71, 72, and 73 may be implemented in the form of a GUI on the main display 121 or the sub display 122.

The display 140 may display the indicator 71 for displaying information about a diagnostic subject (Application). That is, the ultrasonic diagnostic device 40 may provide the user with information about a diagnostic subject related to the ultrasonic image currently displayed on the display 140 through the indicator 71 displayed on the display 140.

For example, when an obstetric examination (e.g., fetal ultrasound) is performed using the ultrasonic diagnostic device 40, the indicator 71 for displaying the information about the diagnostic subject (Application) may include a sub-indicator (e.g., OB in FIG. 7) indicating that an examination for diagnosing the condition of a fetus during pregnancy is performed, a sub-indicator (e.g., CV in FIG. 7) indicating that the diagnostic subject is a cardiovascular mode for diagnosing a heart or blood vessel structure of the fetus, and/or a sub-indicator (e.g., 1-8A in FIG. 7) indicating a type and frequency range of the probe 20 used for the examination.

Also, the display 140 may display the indicator 72 for displaying information about basic indices. That is, the ultrasonic diagnostic device 40 may provide the user with information about the basic indices related to the ultrasonic image currently displayed on the display 140 through the indicator 71 displayed on the display 140.

The basic indices may include at least one of a mechanical index MI and a temperature index TI.

The mechanical index MI, which is a measure exponentially expressing a potential for ultrasound to have a mechanical effect on a tissue, may include information about non-thermal effects that may occur as ultrasound is irradiated. The mechanical index MI may be determined by an amplitude or frequency of the ultrasound irradiated onto the object.

The temperature index TI, which is a scale exponentially expressing a thermal effect that ultrasound applies to the object, may include information about temperature increase effect that may occur when ultrasound is irradiated to the object. The temperature index TI may include at least one of a soft tissue thermal index (TIs) including information about temperature increase in a soft tissue, a bone thermal index (TIb) including information about temperature increase in a tissue adjacent to a bone, and a cranial bone thermal index (TIc) including information about temperature increase in a skull.

Basic index values may be determined based on the diagnostic subject. The types of basic indices and the index values thereof to be indicated for each diagnostic subject may be preset and stored in the memory 150. In addition, the index values of the basic indices may be changed as the user changes setting values when using the ultrasonic diagnostic device 40.

For example, when the obstetric examination (e.g., fetal ultrasound) is performed using the ultrasonic diagnostic device 40, the indicator 72 for displaying the information about the basic indices may include a sub-indicator (e.g., TIs 2.0 in FIG. 7) including the information about temperature increase in the soft tissue, a sub-indicator (e.g., TIb 2.6 in FIG. 7) including the information about temperature increase in the tissue adjacent to the bone, and/or a sub-indicator (e.g., MI 1.0 in FIG. 7) including the information about the non-thermal effects that may occur as ultrasound is irradiated.

Also, the display 140 may display the indicator 73 for displaying a scannable time. That is, the ultrasonic diagnostic device 40 may provide information about the scannable time from the current point in time through the indicator 73 displayed on the display 140. In this case, the scannable time may be preset based on the basic index values and stored in the memory 140.

According to various embodiments, the processor 120 may control the display 140 to not display the indicator 73 for displaying the scannable time based on receiving the user input, on the screen.

The indicator 73 for displaying the scannable time is described in more detail below with reference to FIG. 8.

Figure 8:
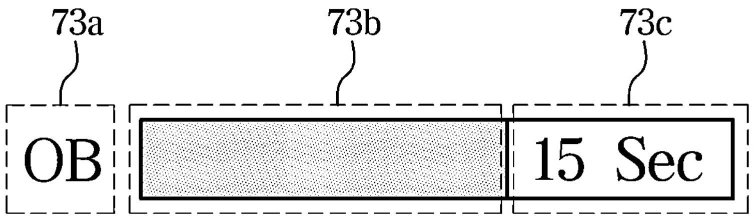
FIG. 8 is a diagram illustrating an indicator providing a scannable time according to an embodiment.

FIG. 8 is a diagram illustrating an indicator providing a scannable time according to an embodiment.

According to an embodiment, the indicator 73 for displaying the scannable time to be displayed on the display 140 of the ultrasonic diagnostic device 40 may include a first sub-indicator 73*a* displaying information about the object or diagnostic subject, a second sub-indicator 73*b* displaying information about a time at which the scan has been performed, and/or a third sub-indicator 73*c* displaying information about a remaining scannable time.

By combining the second sub-indicator 73*b* displaying the information about the time at which the scan has been performed and the third sub-indicator 73*c* displaying information about the remaining scannable time, information about the maximum scannable time for each object or diagnostic subject may be displayed.

The maximum scannable time for each object or diagnostic subject may correspond to the maximum time over which the scan may be performed continuously when the scan for each object or diagnostic subject is performed. The maximum scannable time for each object or diagnostic subject may be preset based on various setting values of the scan object or ultrasonic diagnostic device 40 and stored in the memory 150. Also, when guidelines regarding maximum scan times are updated or country-specific guidelines differ, the maximum scan time for each object or diagnostic subject stored in the memory 150 may be changed by receiving the updated guidelines or country-specific guidelines from an external device (e.g., a server).

In this case, the first sub-indicator 73*a*, the second sub-indicator 73*b* or the third sub-indicator 73*c* may each be included in the indicator 73 providing the information about the scannable time, as a single or multiple units. For example, as illustrated in FIG. 8, the third sub-indicator 73*c*, which displays the information about remaining scannable time for each object, may be implemented as a bar-shaped icon indicator and a text-shaped indicator (e.g., 15 second).

The indicator 73 for displaying the scannable time may improve user visibility by including the first sub-indicator 73*a*, the second sub-indicator 73*b*, or/and the third sub-indicator 73*c*.

Figure 9:
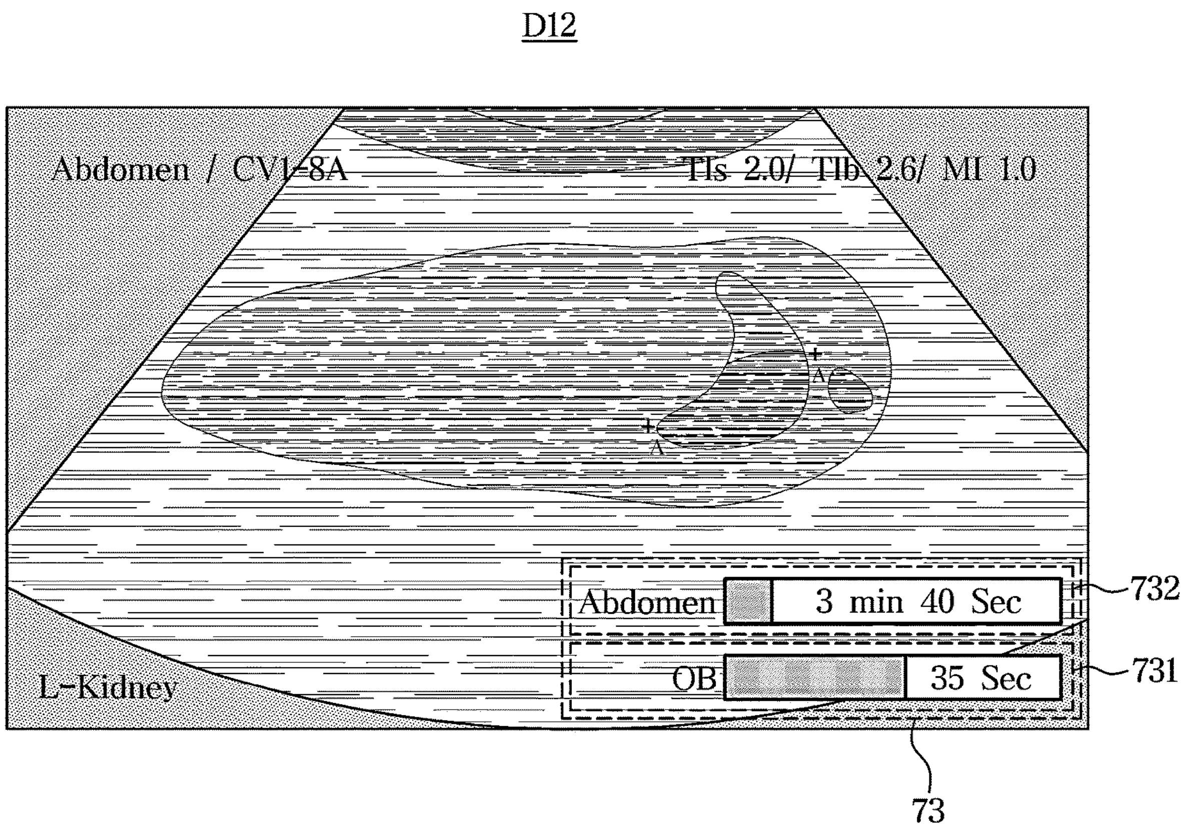
FIG. 9 is a diagram illustrating a screen D12 and a plurality of indicators displayed on the display of the ultrasonic diagnostic device following FIG. 7 according to an embodiment.

FIG. 9 is a diagram illustrating a screen D12 and a plurality of indicators displayed on the display of the ultrasonic diagnostic device following FIG. 7 according to an embodiment.

Figure 10:
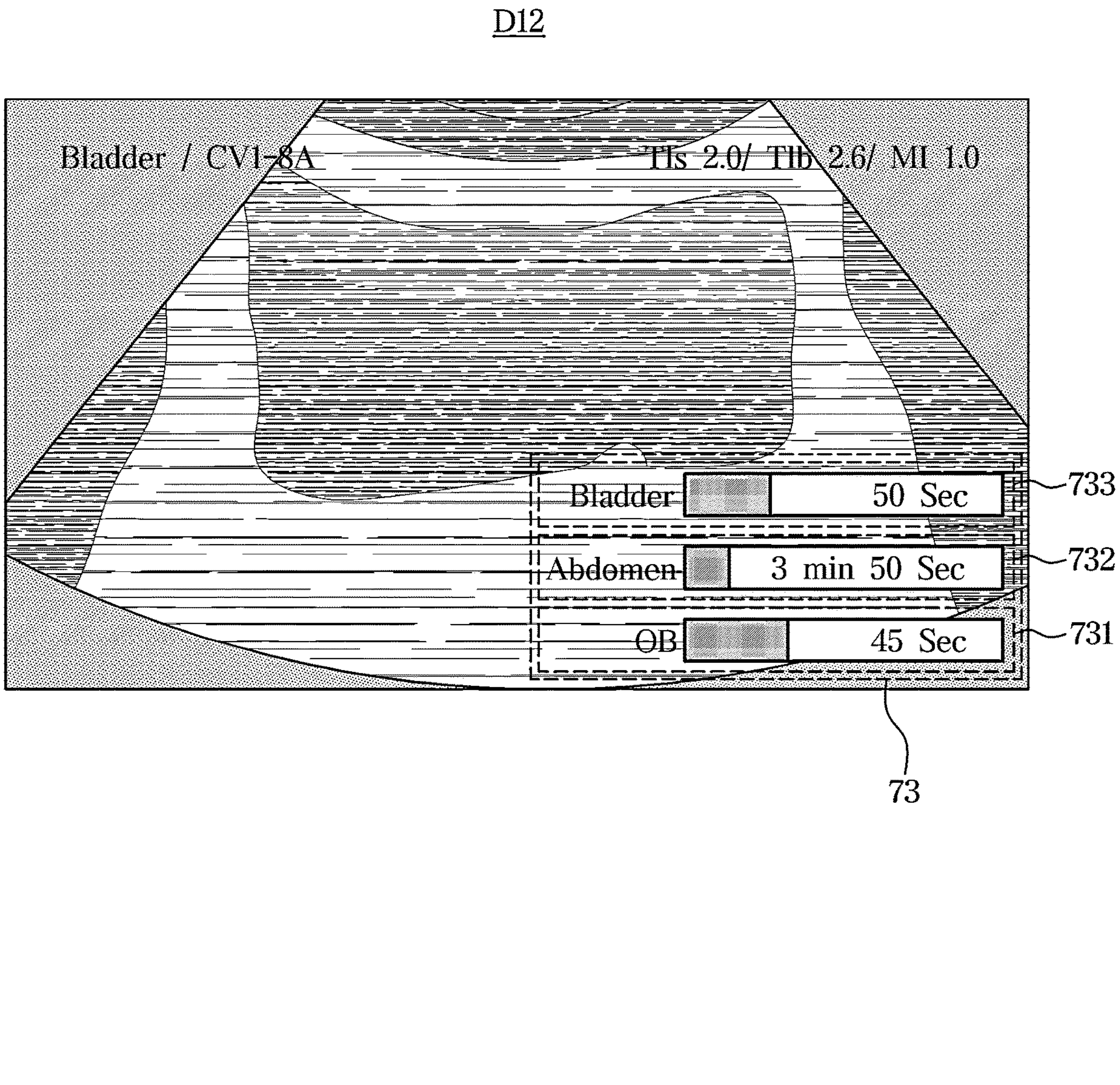
FIG. 10 is a diagram illustrating a screen D13 and a plurality of indicators displayed on the display of the ultrasonic diagnostic device following FIG. 9 according to an embodiment.

FIG. 10 is a diagram illustrating a screen D13 and a plurality of indicators displayed on the display of the ultrasonic diagnostic device following FIG. 9 according to an embodiment.

According to an embodiment, when the user performs an object scan on at least one diagnostic subject, the processor 120 may be changed at least one of the indicators 71, 72, and 73 for displaying a variety of information processed in the ultrasonic diagnostic device 40, which is displayed on the display 140, as the diagnostic subject is changed.

For example, in the obstetric examination, the user may change the diagnostic subject from diagnosis of a fetus (see FIG. 7) to diagnosis of an abdomen of a pregnant woman (see FIG. 9), and then change the diagnostic subject from the diagnosis of the abdomen of the pregnant woman (see FIG. 9) to diagnosis of a bladder of the pregnant woman (see FIG. 10).

According to an embodiment, the processor 120 may modify the indicator 71 for displaying the information about the diagnostic subject (Application) to display information about the changed diagnostic subject.

That is, as the diagnostic subject is changed from the diagnosis of the fetus to diagnosis of the abdomen of the pregnant woman, the processor 120 control the display 140 so that the indicator 71 for displaying the information about the diagnostic subject (Application) includes 'Abdomen' instead of 'OB'. Also, as the diagnostic subject is changed from the diagnosis of the abdomen of the pregnant woman to the diagnosis of the bladder of the pregnant woman, the processor 120 may control the display 140 so that the indicator 71 for displaying the information about the diagnostic subject (Application) includes 'Bladder' instead of 'Abdomen'.

According to an embodiment, as the diagnostic subject is changed, the processor 120 may modify the indicator 72 for displaying the information about a preset basic index corresponding to each diagnostic subject. Changing the indicator 72 for displaying the information about the basic indies may include changing an index value of the mechanical index or the temperature index included in the basic indies. Also, changing the indicator 72 for displaying the information about the basic indies may include changing the type of index included in the temperature index (e.g., Tis, Tib, and Tic).

That is, as the diagnostic subject changed from the diagnosis of the abdomen of the pregnant woman to the diagnosis of the bladder of the pregnant woman, the processor 120 may control the indicator 72 for displaying the information about the basic indies to include 'Tis 2.0/Tib 3.1/MI 1.0' instead of "Tis 2.0/Tib 2.6/MI 1.0".

According to an embodiment, when the user performs the object scan on at least one diagnostic subject, the processor 120 may modify the indicator 73 for displaying the scannable time as the diagnostic subject is changed. That is, as the diagnostic subject is changed, the processor 120 may modify the indicator 73 for displaying the scannable time to include an indicator for displaying the scannable time for the changed diagnostic subject.

Specifically, the processor 120 may sum up scan information for each diagnostic subject and display indicators (731, 732, and 733 in FIGS. 9 and 10) for displaying the scannable time for each diagnostic subject for at least one diagnostic subject on the display device 40.

Specifically, when the user performs the object scan on at least one diagnostic subject, the processor 120 may automatically identify a scan area to determine whether the diagnostic subject has changed. In this case, automatic identification of the scan area may be performed by a machine learning model.

Accordingly, the processor 120 may display the scannable time for the changed diagnostic subject on the display 140. In this case, the processor 120 may display, on the display 140, an indicator for displaying the scannable time for at least one diagnostic subject for which the scan has been performed in the past, together with the indicator for displaying the scannable time for the changed diagnostic subject, in addition to the diagnostic subject currently being scanned (e.g., the changed diagnostic subject).

For example, referring to FIG. 9, as the diagnostic subject is changed from the diagnosis of the fetus to the diagnosis of the abdomen of the pregnant woman, the processor 120 may control the display 140 to display the indicator 732 indicating the scannable time at the diagnosis of the abdomen of the pregnant woman. That is, as the diagnostic subject is changed from the diagnosis of the fetus to the diagnosis of the abdomen of the pregnant woman, the processor 120 may modify the indicator 73 for displaying the scannable time to include the indicator 732 indicating the scannable time at the diagnosis of the abdomen of the pregnant woman.

The processor 120 may also control the display 140 to display the indicator 731 indicating the scannable time at the diagnosis of the fetus performed in the past, in addition to the indicator 732 indicating the scannable time at the diagnosis of the abdomen of the pregnant woman (e.g., the changed diagnostic subject).

Referring to FIG. 10, as the diagnostic subject is changed from the diagnosis of the abdomen of the pregnant woman to the diagnosis of the bladder of the pregnant woman, the processor 120 may also control the display 140 to display the indicator 733 indicating the scannable time at the diagnosis of the bladder of the pregnant woman. That is, as the diagnostic subject is changed from the diagnosis of abdomen of the pregnant woman to the diagnosis of the bladder of the pregnant woman, the processor 120 may modify the indicator 73 for displaying the scannable time to include the indicator 733 indicating the scannable time at the diagnosis of the bladder of the pregnant woman.

The processor 120 may also display an indicator indicating the scannable time for the diagnostic subject performed in the past, in addition to the indicator 733 indicating the scannable time at the diagnosis of the bladder of the pregnant woman (e.g., the changed diagnostic subject). Accordingly, the processor 120 may control the display 140 to display the indicator 731 indicating the scannable time at the diagnosis of the fetal and the indicator 732 indicating the scannable time at the diagnosis of the abdomen of the pregnant woman together.

That is, as the diagnostic subject is changed, the processor 120 may modify the indicator 73 for displaying the scannable time to include the indicator for displaying the scannable time for the changed diagnostic subject and/or at least one indicator for displaying the scannable time for at least one diagnostic subject performed in the past.

Figure 11:
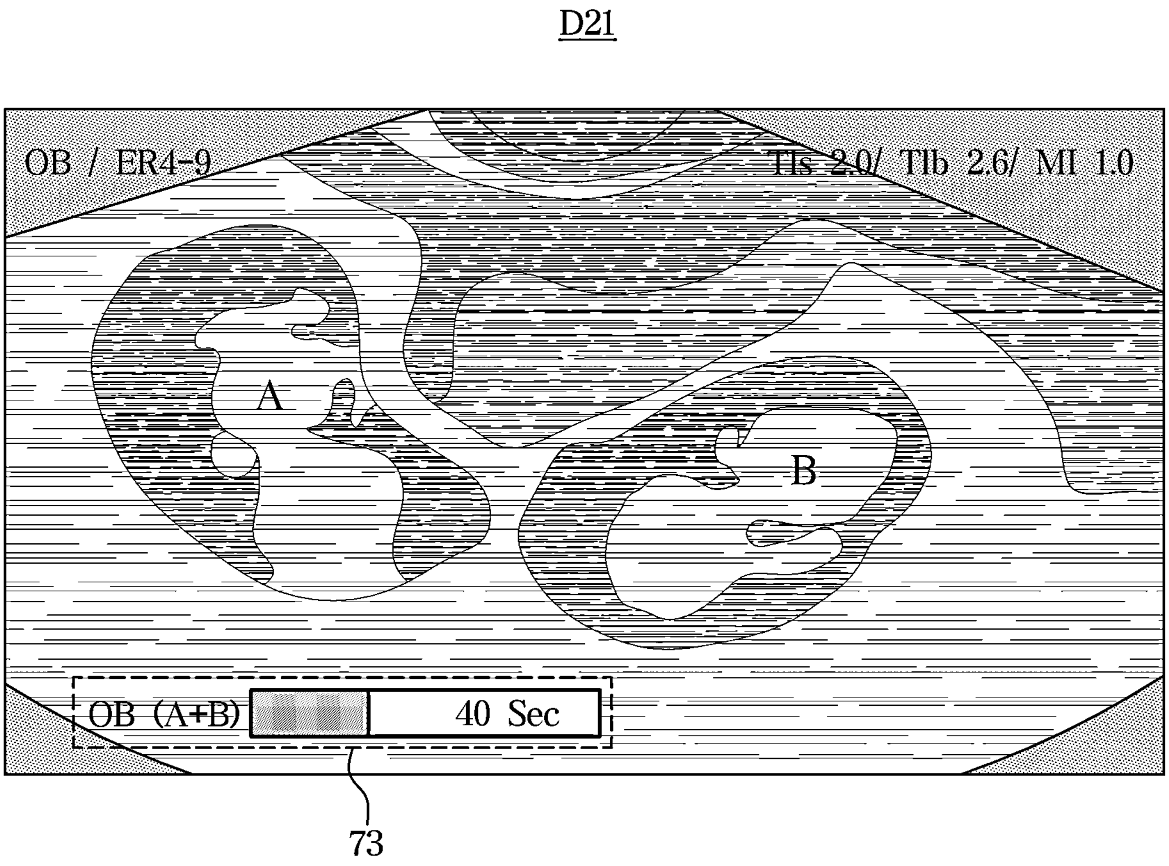
FIG. 11 is a diagram illustrating a screen D21 and a plurality of indicators displayed on the display of the ultrasonic diagnostic device according to another embodiment.

FIG. 11 is a diagram illustrating a screen D21 and a plurality of indicators displayed on the display of the ultrasonic diagnostic device according to another embodiment.

Figure 12:
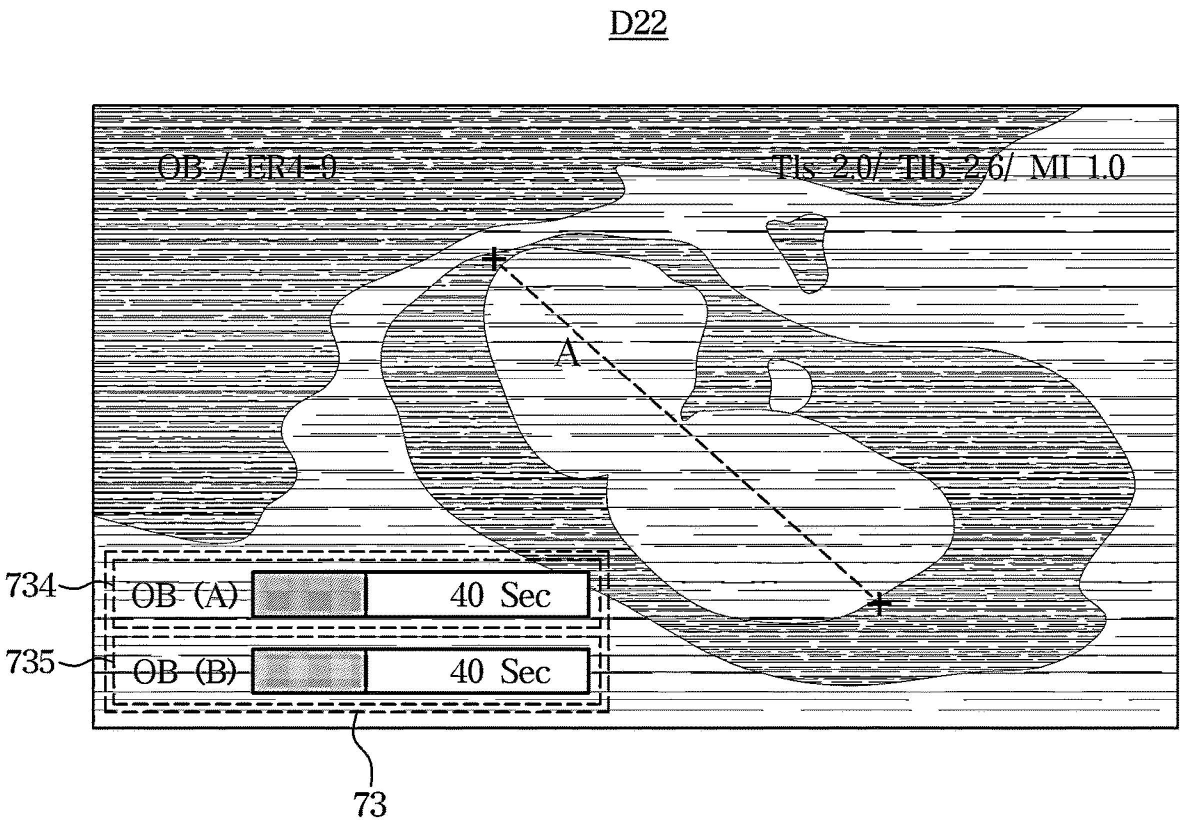
FIG. 12 is a diagram illustrating a screen D22 and a plurality of indicators displayed on the display of the ultrasonic diagnostic device following FIG. 11 according to another embodiment.

FIG. 12 is a diagram illustrating a screen D22 and a plurality of indicators displayed on the display of the ultrasonic diagnostic device following FIG. 11 according to another embodiment.

Figure 13:
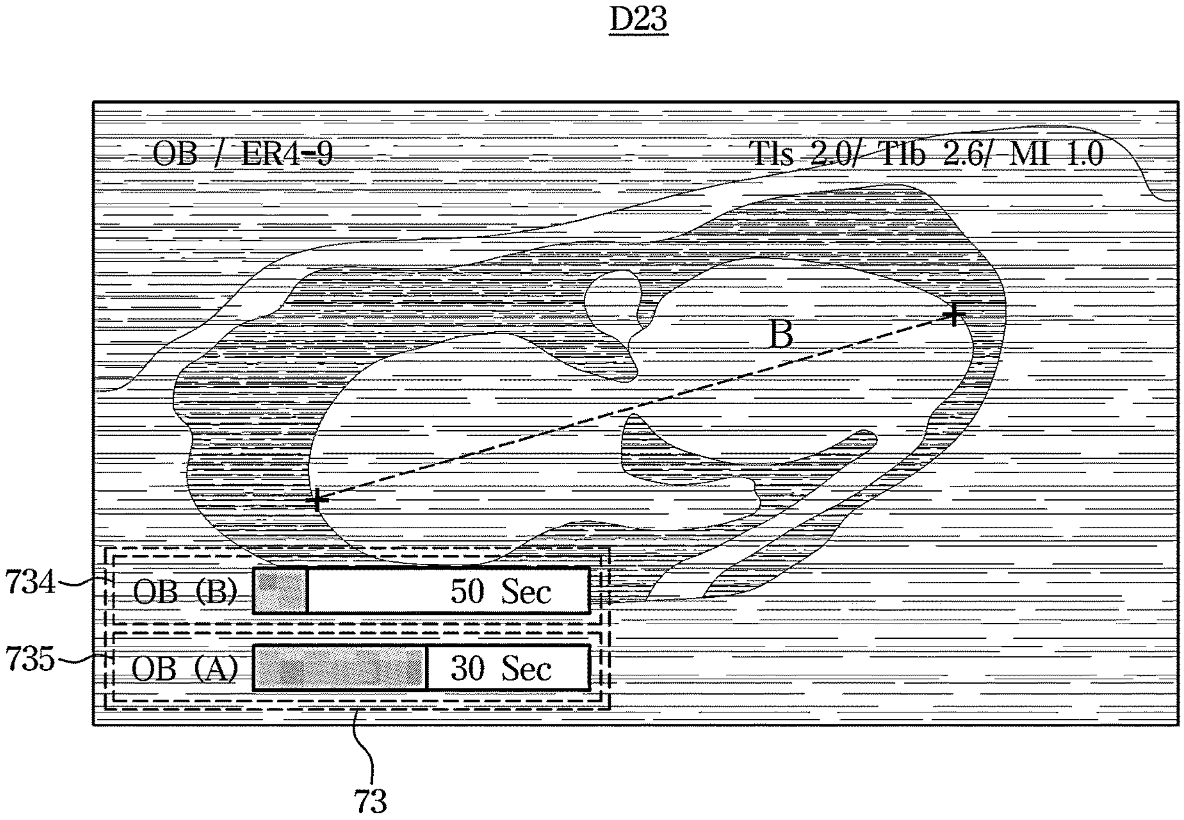
FIG. 13 is a diagram illustrating a screen D23 and a plurality of indicators displayed on the display of the ultrasonic diagnostic device following FIG. 12 according to another embodiment.

FIG. 13 is a diagram illustrating a screen D23 and a plurality of indicators displayed on the display of the ultrasonic diagnostic device following FIG. 12 according to another embodiment.

According to an embodiment, when the user performs a scan on at least one object, the processor 120 may modify at least one of the indicators 71, 72, and 73 for displaying a variety of information processed in the ultrasonic diagnostic device 40 that is displayed on the display 140 as the object is changed.

According to an embodiment, when the user performs a scan on at least one object, the processor 120 may modify the indicator 73 for displaying the scannable time as the object is changed. That is, the processor 120 may modify the indicator 73 for displaying the scannable time to include the indicator for displaying the scannable time for the changed object as the object is changed.

For example, in the obstetric examination, when an examination on twins is performed, while a scan is being performed on both the twins as an object (see FIG. 11), the scan object may be changed to one fetus of the twins (hereinafter referred to as object A) (FIG. 12), and then while a scan is being performed on the one fetus of the twins, the scan object may be changed to the other fetus of the twins (hereinafter referred to as object B) (FIG. 13).

According to an embodiment, when the user performs a scan on at least one object, the processor 120 may modify the indicator 73 for displaying the scannable time as the object is changed. That is, the processor 120 may modify the indicator 73 for displaying the scannable time to include the indicator for displaying the scannable time for the changed object as the object is changed.

Specifically, when the scannable time for a plurality of the objects is the same, the processor 120 may display the indicator for displaying the scannable time for the plurality of objects as a single indicator.

For example, referring to FIG. 11, when the examination of the twins is performed and both the twins are scanned as the object, times at which scans are performed for the respective twins (e.g., the object A and object B) may be the same, and thus the remaining scannable time for each object may also be the same.

Accordingly, the processor 120 may modify the first sub-indicator 73*a*, which displays information about the object currently being scanned, among the sub-indicators of the indicator 73 for displaying the scannable time to include information that both the twins are being scanned as the object.

For example, as illustrated in FIG. 11, the first sub-indicator 73*a*, which displays the information about the object currently being scanned, may include 'OB(A+B)'. The processor 120 may display identifiers for identifying each object (e.g., the object A and object B) on an ultrasonic image.

The processor 120 may also display, on the display 140, each of the indicators (734 and 735 in FIGS. 12 and 13) for displaying the scannable time for each object for at least one object by summing up the scan information for each object as the scan object is changed.

Specifically, when the user performs a scan on at least one object, the processor 120 may determine whether the object has been changed by automatically identifying the scan area. In this case, the automatic identification of the scan area may be performed by the machine learning model.

Accordingly, the processor 120 may display the scannable time for the changed object on the display 140. In this case, the processor 120 may display, on the display 140, an indicator for displaying the scannable time for at least one object for which the scan has been performed in the past, together with the indicator for displaying the scannable time for the changed object, in addition to the object currently being scanned (e.g., the changed object).

For example, referring to FIG. 12, as the scan object is changed from both the twins (e.g., the object A and object B) to the object A, the processor 120 may control the display 140 to display the indicator 734 indicating the scannable time for the object A. That is, as the scan object is changed from both the twins (e.g., the object A and object B) to the object A, the processor 120 may modify the indicator 734 for displaying the scannable time to include the indicator 734 indicating the scannable time for the object A.

The processor 120 may also control the display 140 to display the indicator 735 indicating the scannable time for the object B for which the scan has been performed in the past, in addition to the indicator 734 indicating the scannable time for the object A (e.g., the changed object).

Referring to FIG. 13, as the scan object is changed from the object A to the object B, the processor 120 may also control the display 140 to display the indicator 735 indicating the scannable time for the object B. That is, as the scan object is changed from the object A to the object B, the processor 120 may modify the indicator 73 for displaying the scannable time to include the indicator 735 indicating the scannable time for the object B.

The processor 120 may also control the display 140 to display the indicator 734 indicating the scannable time for the object A for which the scan has been performed in the past, in addition to the indicator 735 indicating the scannable time for the object B.

That is, as the scan object is changed, the processor 120 may modify the indicator 73 for displaying the scannable time to include the indicator for displaying the scannable time for the changed object and/or at least one indicator for displaying the scannable time for at least one object performed in the past.

Figure 14:
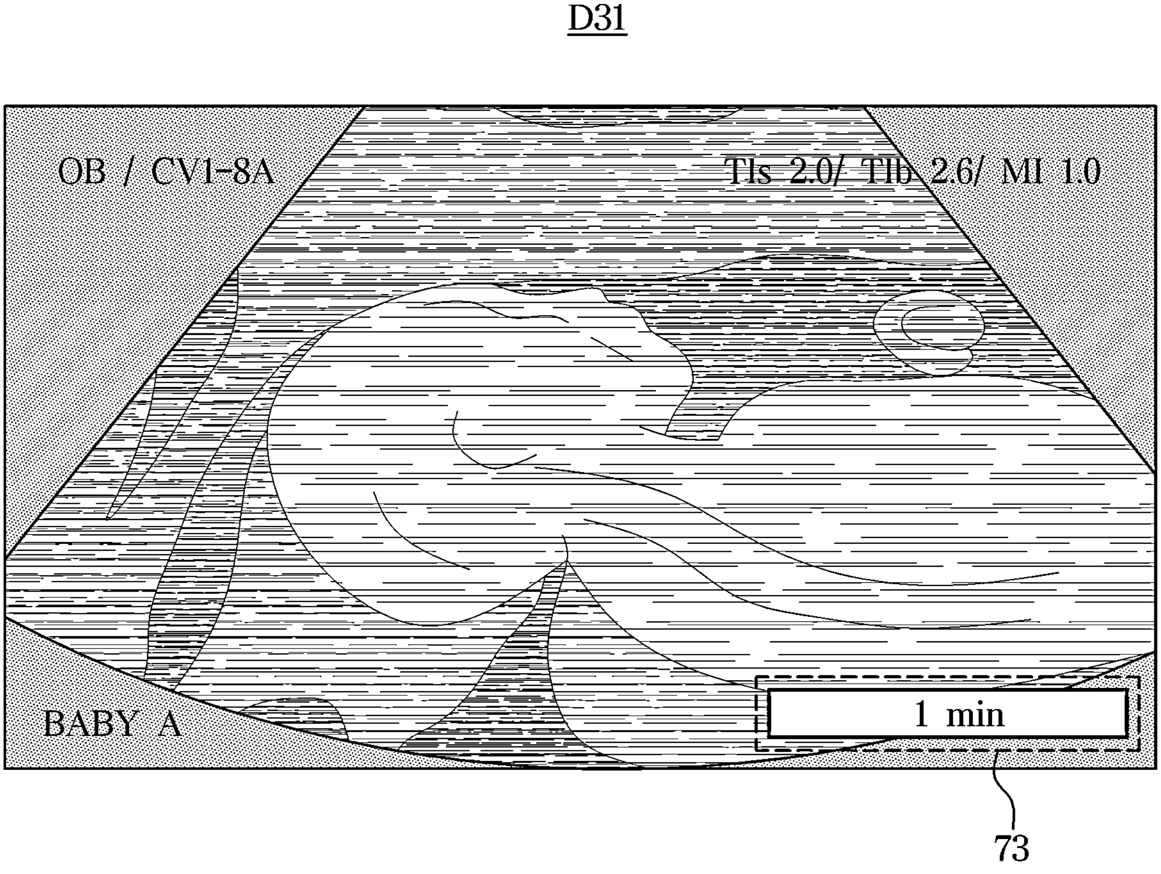
FIG. 14 is a diagram illustrating an example of a screen D31 and a plurality of indicators displayed on the display of the ultrasonic diagnostic device according to another embodiment.

FIG. 14 is a diagram illustrating an example of a screen D31 and a plurality of indicators displayed on the display of the ultrasonic diagnostic device according to another embodiment.

Figure 15:
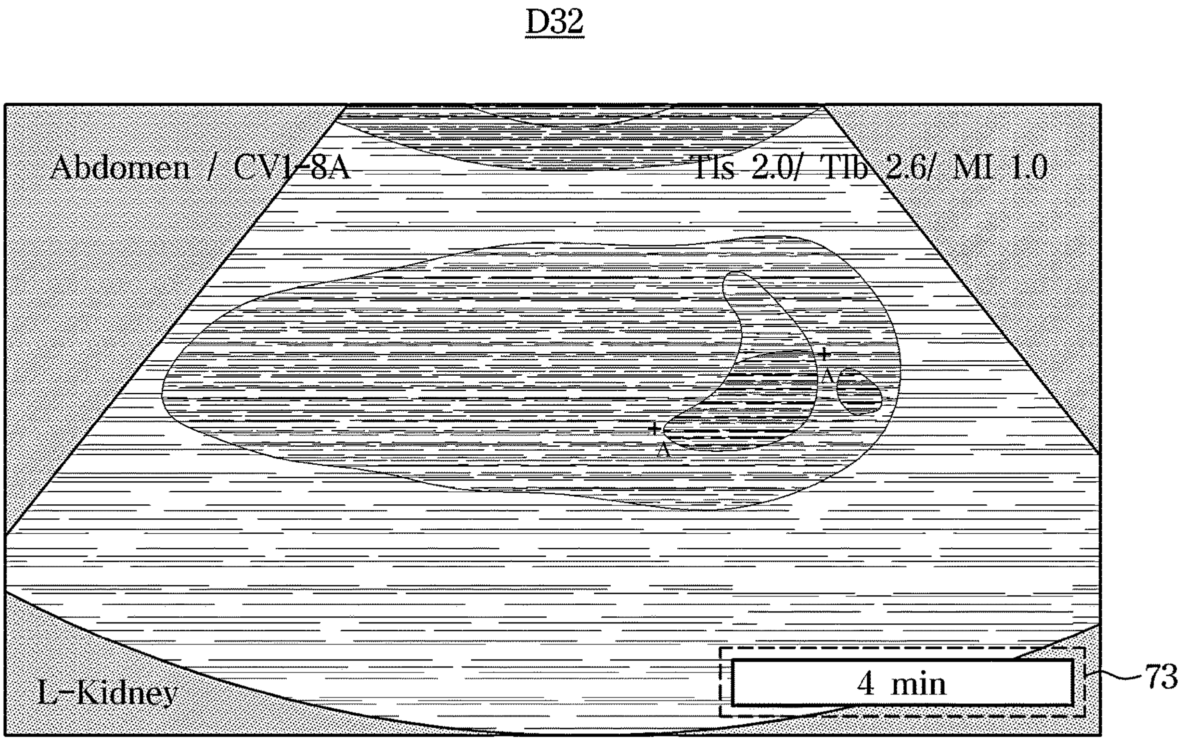
FIG. 15 is a diagram illustrating an example of a screen D32 and a plurality of indicators displayed on the display of the ultrasonic diagnostic device according to another embodiment.

FIG. 15 is a diagram illustrating an example of a screen D32 and a plurality of indicators displayed on the display of the ultrasonic diagnostic device according to another embodiment.

The processor 120 may identify an object in an ultrasonic image corresponding to the scan area and determine whether at least one of the diagnostic subject and object has been changed. In this case, the identification of the object in the ultrasonic image may be performed by the machine learning model.

The processor 120 may extract 'area information', which is information about an area occupied within an ultrasonic image by each of a plurality of objects included in the ultrasonic image obtained based on an echo signal from the scan area received from the ultrasonic transmission/reception module 110.

The processor 120 may classify the plurality of objects included in the ultrasonic image corresponding to the scan area into preset classes based on the extracted area information. The class may mean a cluster classified based on preset criteria in order to identify a specific part, organ, tissue of a body or a fetus classified according to clinical significance. Information about objects included in each of the classes may be preset and stored in the memory 150.

The processor 120 may automatically identify the scan area based on the classes into which the plurality of objects included in the ultrasonic image corresponding to the scan area is classified.

For example, the processor 120 may extract the area information occupied within the ultrasonic image by a head of the fetus, a right hand of the fetus, a left hand of the fetus, a right foot of the fetus, and a left foot of the fetus in the ultrasonic image corresponding to the scan area. Accordingly, the processor 120 may classify the head of the fetus, the right hand of the fetus, the left hand of the fetus, the right foot of the fetus, and the left foot of the fetus into classes for identifying the body of the fetus based on preset criteria. Accordingly, the processor 150 may identify the scan area as containing the fetus.

The operations of segmenting and detecting a plurality of objects included in the ultrasonic image and then classifying the plurality of objects by class may be performed according to various known methods.

For example, the operation of segmenting and detecting a plurality of objects from the ultrasonic image and the operation of classifying the plurality of objects by class may be performed by machine learning. Any one of a plurality of known machine learning models may be used for the machine learning operation. Specifically, neural network-based convolutional neural networks (CNNs), recurrent neural networks (RNNs), LSTM, encoder-decoder, auto-encoder, and generative adversarial networks (GANs) models may be used.

As another example, the operations of detecting a plurality of objects and classifying the plurality of objects into classes may be performed by the 'semantic segmentation' method. 'Semantic segmentation' may mean a method of dividing objects that have specific meanings within the objects. The processor 120 may learn, based on a predetermined algorithm, which class among the plurality of classes a specific part, organ, tissue of the body, or the fetus corresponds to. The processor 120 may detect and segment each of the plurality of objects from three-dimensional volume data of the object based on the learned result. The processor 120 may classify each of a plurality of detected objects into a predetermined class based on the learned result and class information stored in a separate memory 150.

In the obstetric examination, when ultrasound is irradiated on the pregnant woman, both the pregnant woman and the fetus may be scanned. In this case, the processor 120 may determine whether the pregnant woman or the fetus is included within the scan area. That is, the processor 120 may identify the object included in the ultrasonic image.

The processor 120 may determine the diagnostic subject for scanning the fetus when the fetus is included within the scan area. The diagnostic subject for scanning the identified object may be preset and stored in the memory 150. That is, the processor 120 may determine the diagnostic subject based on the fetus being identified in the ultrasound image.

The diagnostic subject may be changed by the user before or during the scan. That is, the processor 120 may determine the diagnostic subject to scan the identified object based on at least one of the user inputs for the identified object or diagnostic subject.

The processor 120 may control the display 140 to display the indicator 73 for displaying the scannable time at the fetal diagnosis determined based on the preset basic index based on the object or the diagnostic subject of the object.

For example, as illustrated in FIG. 14, the processor 120 may determine that the maximum scannable time for the fetus may be 1 minute based on the TIb being set to 2.6 as the diagnostic subject is determined to be 'OB'. Accordingly, because the fetal scan has not yet been performed, the processor 120 may display, on the display 140, the indicator 73 for displaying the scannable time so that the third sub-indicator 73*c* displaying information about the remaining scannable time for the fetus may indicate 1 minute.

The processor 120 may also control the display 140 to display at least one of the indicator 71 for displaying information about a determined diagnostic subject and the indicator 72 for displaying information about the basic indies together with the indicator 73 for displaying the scannable time.

The processor 120 may determine the diagnostic subject for scanning the pregnant woman when the pregnant woman is included within the scan area. The diagnostic subject for scanning the pregnant woman may be preset and stored in the memory 150. That is, the processor 120 may determine the diagnostic subject based on the pregnant woman being identified in the ultrasound image.

The diagnostic subject may be changed by the user before or during the scan. That is, the processor 120 may determine the diagnostic subject to scan the identified object based on at least one of the user inputs for the identified object or diagnostic subject.

When the diagnostic subject for scanning the pregnant woman is determined, the processor 120 may control the display 140 to display the indicator 73 for displaying the scannable time at the diagnosis of the pregnant woman determined based on the preset basic index.

For example, as illustrated in FIG. 15, the processor 120 may determine that the maximum scannable time for the abdomen of the pregnant woman may be 4 minutes based on the TIb being set to 2.6 as the diagnostic subject is determined to be 'Abdomen' of the pregnant woman. Accordingly, because the pregnant woman scan has not yet been performed, the processor 120 may display, on the display 140, the indicator 73 for displaying the scannable time so that the third sub-indicator 73*c* displaying information about the remaining scannable time for the abdomen of the pregnant woman may indicate 4 minutes.

The processor 120 may also control the display 140 to display at least one of the indicator 71 for displaying the information about the determined diagnostic subject and the indicator 72 for displaying the information about the basic indies together with the indicator 73 for displaying the scannable time.

Figure 16:
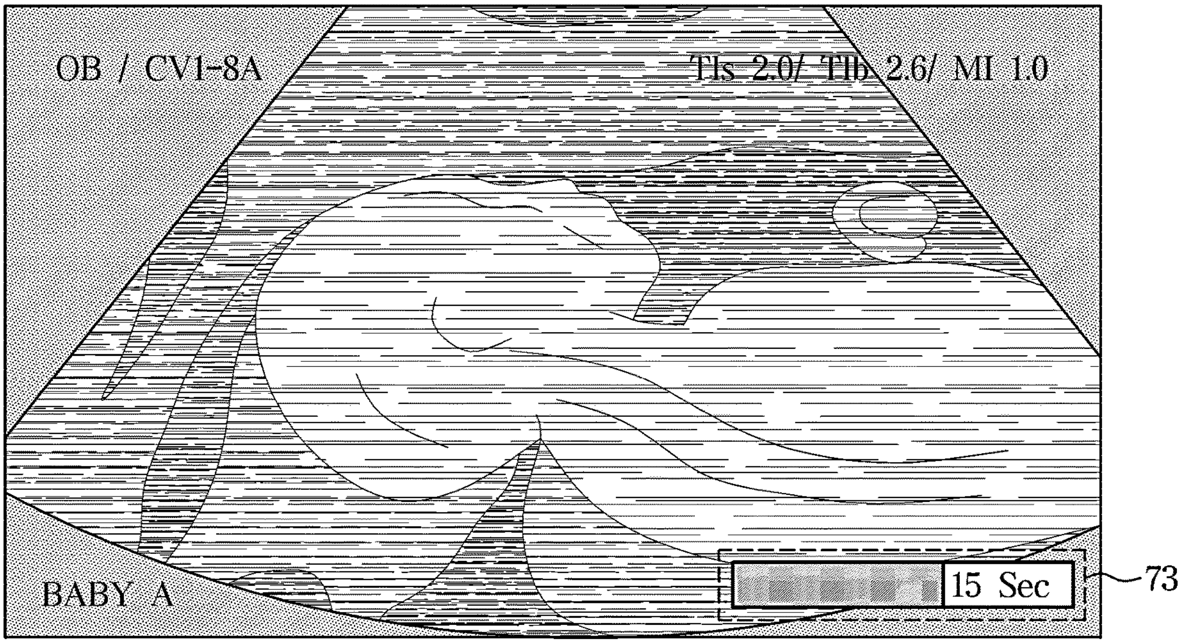
FIG. 16 is a diagram illustrating a screen D33 and a plurality of indicators displayed on the display of the ultrasonic diagnostic device following FIG. 14 according to another embodiment.

FIG. 16 is a diagram illustrating a screen D33 and a plurality of indicators displayed on the display of the ultrasonic diagnostic device following FIG. 14 according to another embodiment.

As described above with reference to FIG. 15, the processor 120 may determine the diagnostic subject for scanning the fetus based on the fetus being determined to be included in the scan area (e.g., based on the fetus being identified in the ultrasound image), and may display, on the display 140, the indicator 73 for providing the information about the maximum scan time for the fetus based on the basic indies preset before the scan is performed.

As the scan of the object is initiated by the user and the scan time for the object elapses, the scannable time for the object currently being scanned decreases.

In this case, as the scan time for the object elapses, the processor 120 may modify the second sub-indicator 73*b* and the third sub-indicator 73*c* to update and display the information about the time at which the scan has been performed and the remaining scannable time.

For example, as illustrated in FIG. 16, when the scan of the fetus is performed for 45 seconds, the processor 120 may modify the indicator 73 for displaying the scannable time to increase a length of a bar of the second sub-indicator 73*b* displaying the information about the time at which the scan for each object has been performed and decrease a length of a bar of the third sub-indicator 73*c* displaying the information about the remaining scannable time for each object. In addition, an indicator of a character form included in the third sub-indicator 73*c* may also be changed from 1 minute to 15 seconds decreased by the amount of time it took to perform the scan (for example, 45 seconds).

As the object scan is performed, the processor 120 may also modify the second sub-indicator 73*b* and the third sub-indicator 73*c* to update and display information about the remaining scannable time based on a change in the index values of the basic indies due to a change in the setting values of the ultrasonic diagnostic device 40.

For example, as an output value of the ultrasonic probe 20 increases, an index value of the temperature index TI may increase. Accordingly, the maximum scannable time for the object may decrease.

In this case, the processor 120 may modify the indicator 73 for displaying the scannable time so that the length of the bar of the third sub-indicator 73*c*, which displays the information about the remaining scannable time for each object based on the changed index value of the temperature index TI, relatively decreases. In this case, the length of the bar of the second sub-indicator 73*b*, which displays the information about the time at which the scan for each object has been performed, may be displayed as if it is relatively increasing. In addition, the indicator of the character form included in the third sub-indicator 73*c* may also be changed from 1 minute to 15 seconds decreased by an amount of decreased time (for example, 45 seconds) as the index value of the temperature index TI increases.

In other words, the processor 120 may modify the indicator 73 for displaying the scannable time to display the scannable time updated based on accumulated scan time as the scan is performed.

The processor 120 may also modify the indicator 73 for displaying the scannable time to display the scannable time updated based on the index values of the basic indies changed in a process in which the scan is performed.

Figure 17:
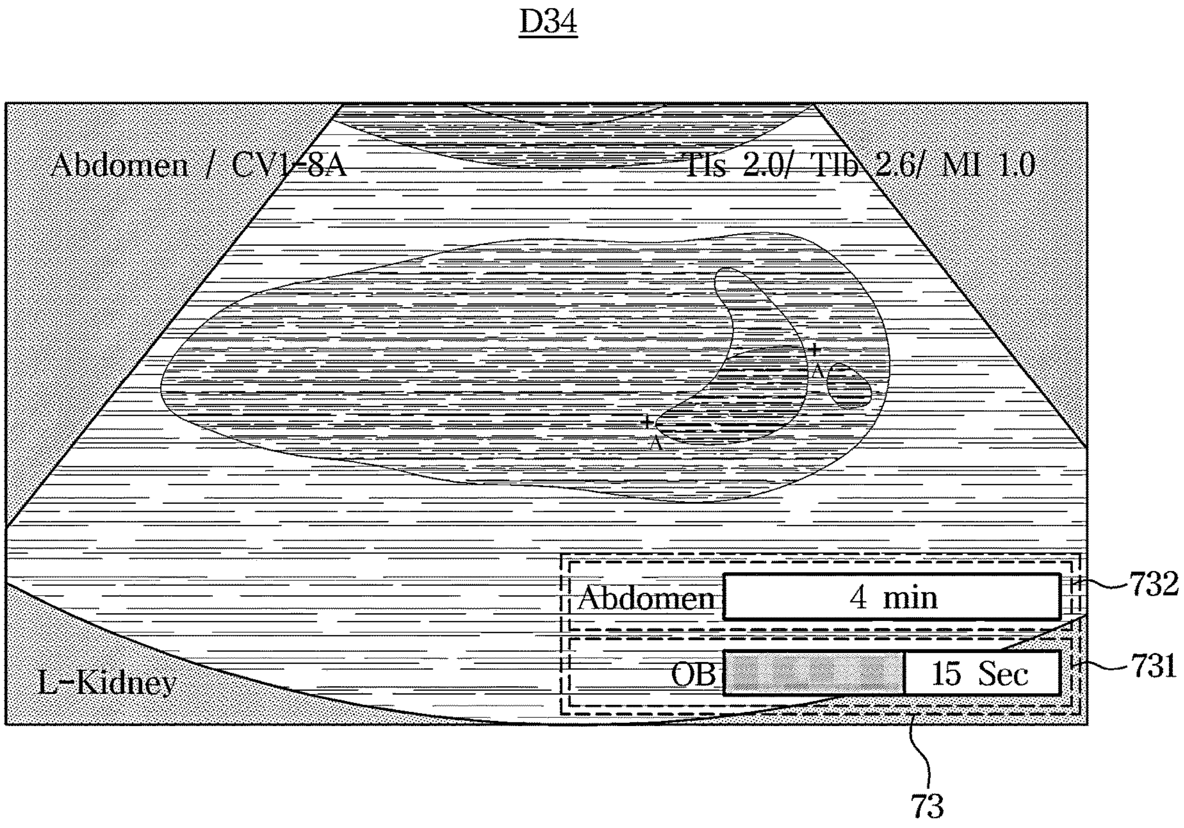
FIG. 17 is a diagram illustrating a screen D34 and a plurality of indicators displayed on the display of the ultrasonic diagnostic device following FIG. 16 according to another embodiment.

FIG. 17 is a diagram illustrating a screen D34 and a plurality of indicators displayed on the display of the ultrasonic diagnostic device following FIG. 16 according to another embodiment.

Figure 18:
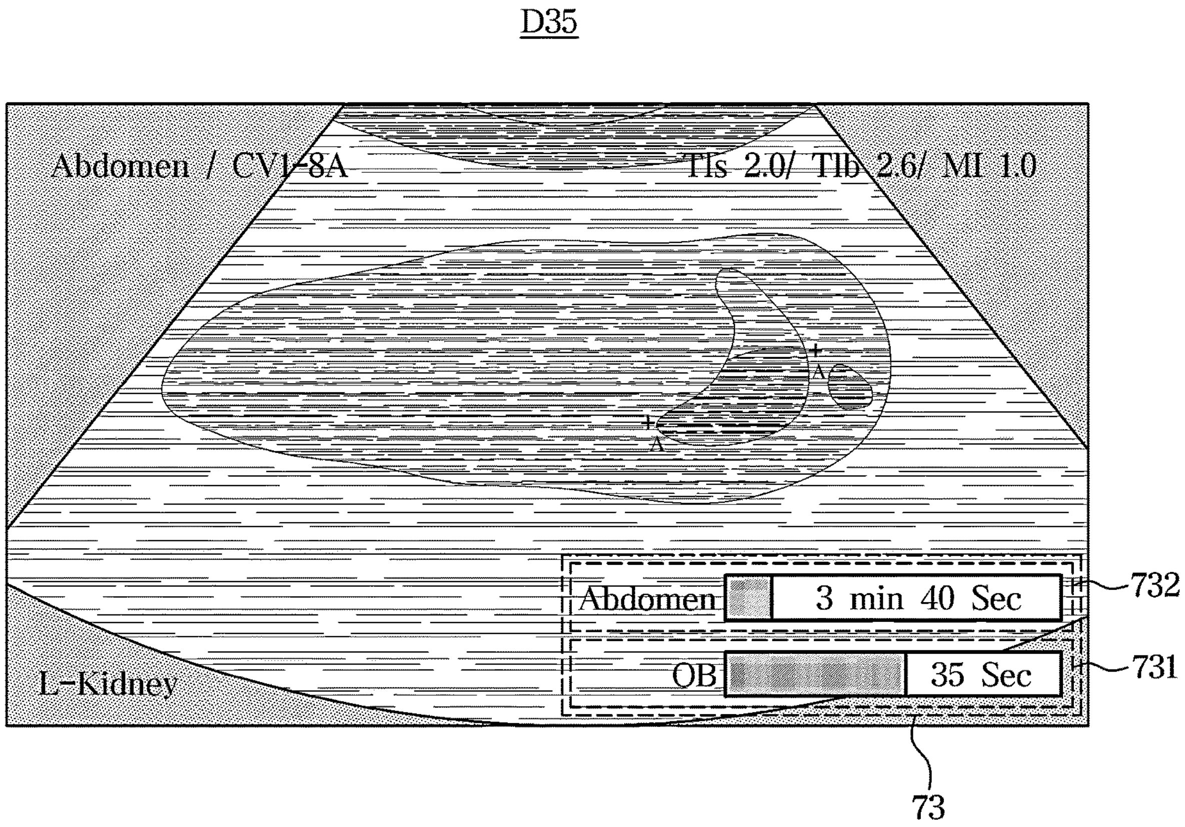
FIG. 18 is a diagram illustrating a screen D35 and a plurality of indicators displayed on the display of the ultrasonic diagnostic device following FIG. 17 according to another embodiment.

FIG. 18 is a diagram illustrating a screen D35 and a plurality of indicators displayed on the display of the ultrasonic diagnostic device following FIG. 17 according to another embodiment.

The processor 120 may modify the indicator 73 for displaying the scannable time based on the object being changed in the process in which the scan is performed. That is, as the object is changed, the processor 120 may control the indicator 73 for displaying the scannable time to include the indicator for displaying the scannable time for the changed object.

For example, as the scan for the fetus is performed for 45 seconds and the object is changed to the abdomen of a pregnant woman, the processor 120 may modify the indicator 73 for displaying the scannable time to be displayed on the display 140 as illustrated in FIG. 17.

According to an embodiment, as the object is changed, the processor 120 may modify the indicator 73 for displaying the scannable time to include the indicator for displaying the scannable time for the changed object. In other words, as the object is changed, the processor 120 may modify the indicator 73 for displaying the scannable time to include an indicator for displaying the scannable time for the object currently being scanned. For example, the processor 120 may display, on the display 140, the indicator 732 for displaying the scannable time for the abdomen of the pregnant woman, which is the object currently being scanned.

In this case, the processor 120 may display, on the display 140, the indicator for displaying the scannable time for at least one object for which the scan has been performed in the past, together with the indicator for displaying the scannable time for the changed object, in addition to the object currently being scanned (e.g., the changed object). That is, the processor 120 may modify the indicator 73 for displaying the scannable time so that the indicator 73 for displaying the scannable time includes the indicator for displaying the scannable time for the object currently being scanned and at least one indicator for displaying the scannable time for at least one object for which the scan has been performed before the object is changed.

For example, referring to FIG. 17, the processor 120 may display, on the display 140, the indicator 731 for displaying the scannable time for the fetus for which the scan has been performed before changing the scan object to the abdomen of the pregnant woman.

As the scan is performed after the object is changed, the processor 120 may modify the second sub-indicator 73*b* and the third sub-indicator 73*c* among the sub-indicators of the indicator 73 for displaying the scannable time to update and display the information about the time at which the scan of the changed object has been performed and the remaining scannable time. That is, as the scan is performed after the object is changed, the processor 120 may control the display 140 so that the indicator 73 for displaying the scannable time for the changed object includes an indicator for displaying an updated scannable time for the object.

The processor 120 may also modify the second sub-indicator 73*b* and the third sub-indicator 73*c* among the sub-indicators of the indicator 73 for displaying the scannable time to update and display information about the remaining scannable time for at least one object for which the scan has been performed in the past before the object is changed. That is, as the scan is performed after the object is changed, the processor 120 may control the display 140 so that the indicator 73 for displaying the scannable time includes an indicator for displaying an updated scannable time for at least one object for which the scan has been performed in the past. In this case, updating the information about the remaining scannable time for at least one object for which the scan has been performed in the past before the object is changed may include increasing the remaining scannable time for at least one object for which the scan has been performed in the past during a time at which the scan of the changed object has been performed.

For example, as the scan is performed for 20 seconds after the scan object is changed to the abdomen of the pregnant woman, the processor 120 may modify the indicator 73 for displaying the scannable time to be displayed on the display 140 as illustrated in FIG. 18.

For example, as illustrated in FIG. 18, as the scan for the abdomen of the pregnant woman is performed for 20 seconds, the processor 120 may modify the indicator 73 for displaying the scannable time to increase the length of the bar of the second sub-indicator 73*b* displaying the information about the time at which the scan has been performed and decrease the length of the bar of the third sub-indicator 73*c* displaying the information about the remaining scannable time for each object, among the sub-indicators of the indicator 732 for displaying the scannable time for the abdomen of the pregnant woman. In addition, the indicator of the character form included in the third sub-indicator 73*c* may also be changed from 4 minutes, which is the maximum scannable time, to 3 minutes and 40 seconds decreased by an amount of time it took to perform the scan (for example, 20 seconds).

The processor 120 may also modify the indicator 73 for displaying the scannable time to increase the length of the bar of the third sub-indicator 73*c* displaying the information about the remaining scannable time for each object among the sub-indicators of the indicator 731 for displaying the scannable time for the fetus. Accordingly, the processor 120 may display the length of the bar of the second sub-indicator 73*b*, which displays the information about the time at which the scan has been performed among the sub-indicators of the indicator 731 for displaying the scannable time for the fetus, as if it has decreased. In addition, the indicator of the character form included in the third sub-indicator 73*c* may also change the remaining scannable time from 15 seconds to 45 seconds increased by an amount of time it took to perform the abdomen scan of the pregnant woman (for example, 20 seconds).

Figure 19:
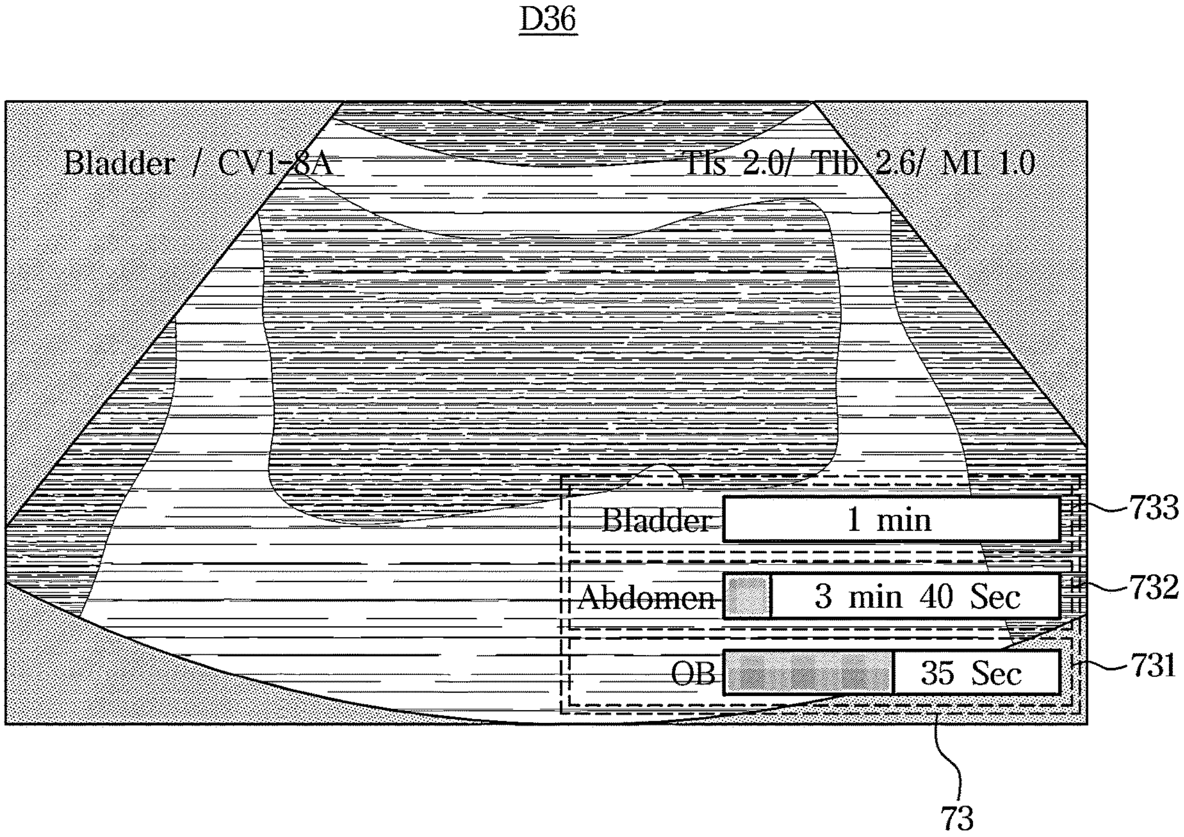
FIG. 19 is a diagram illustrating a screen D36 and a plurality of indicators displayed on the display of the ultrasonic diagnostic device following FIG. 18 according to another embodiment.

FIG. 19 is a diagram illustrating a screen D36 and a plurality of indicators displayed on the display of the ultrasonic diagnostic device following FIG. 18 according to another embodiment.

Figure 20:
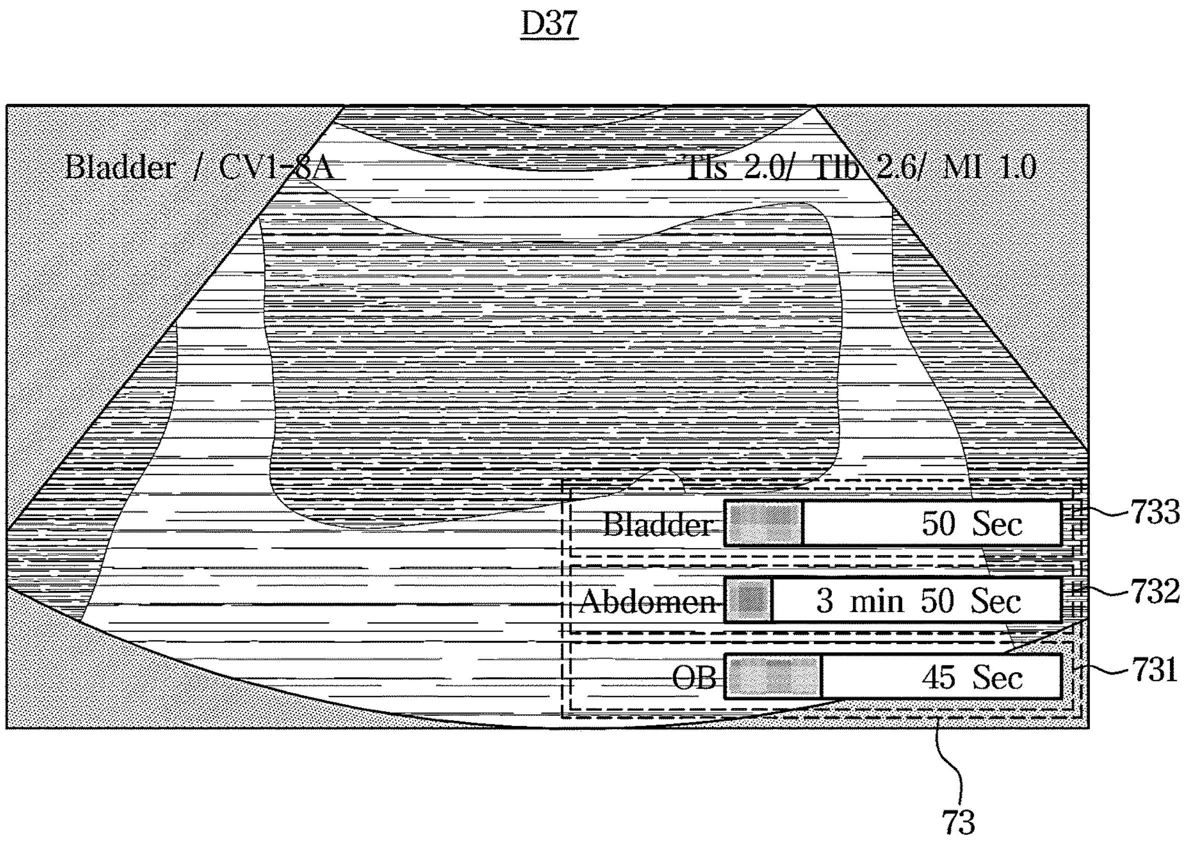
FIG. 20 is a diagram illustrating a screen D37 and a plurality of indicators displayed on the display of the ultrasonic diagnostic device following FIG. 19 according to another embodiment.

FIG. 20 is a diagram illustrating a screen D37 and a plurality of indicators displayed on the display of the ultrasonic diagnostic device following FIG. 19 according to another embodiment.

The processor 120 may modify the indicator 73 for displaying the scannable time based on a change in the diagnostic subject in the process in which the scan is performed. That is, as the diagnostic subject is changed, the processor 120 may control the indicator 73 for displaying the scannable time to include the indicator for displaying the scannable time for the changed diagnostic subject.

For example, as the scan for the abdomen of the pregnant woman is performed for 20 seconds and the diagnostic subject is changed to the bladder of the pregnant woman, the processor 120 may modify the indicator 73 for displaying the scannable time to be displayed on the display 140 as illustrated in FIG. 19.

According to an embodiment, as the diagnostic subject is changed, the processor 120 may modify the indicator 73 for displaying the scannable time to include the indicator for displaying the scannable time for the changed diagnostic subject. In other words, as the diagnostic subject is changed, the processor 120 may modify the indicator 73 for displaying the scannable time to include an indicator for displaying the scannable time for the diagnostic subject currently being scanned. For example, the processor 120 may display, on the display 140, the indicator 733 for displaying the scannable time for the bladder of the pregnant woman, which is the currently selected diagnostic subject.

In this case, the processor 120 may display, on the display 140, the indicator for displaying the scannable time for at least one object for which the scan has been performed in the past, together with the indicator for displaying the scannable time for the changed diagnostic subject, in addition to the currently selected diagnostic subject (e.g., the changed diagnostic subject). That is, the processor 120 may modify the indicator 73 for displaying the scannable time to include an indicator for displaying the scannable time for the currently selected diagnostic subject and at least one indicator for displaying the scannable time for at least one diagnostic subject for which the scan has been performed before the diagnostic subject is changed.

For example, referring to FIG. 19, the processor 120 may display, on the display 140, the indicator 732 for displaying the scannable time for the abdomen of the pregnant woman for which the scan has been performed before changing the diagnostic subject to the bladder of the pregnant woman, together with the indicator 733 for displaying the scannable time for the bladder of a pregnant woman.

As the scan is performed after the diagnostic subject is changed, the processor 120 may modify the second sub-indicator 73*b* and the third sub-indicator 73*c* among the sub-indicators of the indicator 73 for displaying the scannable time to update and display information about a time at which the scan for the changed diagnostic subject has been performed and the remaining scannable time. That is, as the scan is performed after the diagnostic subject is changed, the processor 120 may control the display 140 so that the indicator 73 for displaying the scannable time for the changed diagnostic subject includes an indicator for displaying an updated scannable time for the changed diagnostic subject.

The processor 120 may also modify the second sub-indicator 73*b* and the third sub-indicator 73*c* among the sub-indicators of the indicator 73 for displaying the scannable time to update and display information about the remaining scannable time for at least one diagnostic subject for which the scan has been performed in the past before the diagnostic subject is changed. That is, as the scan is performed after the diagnostic subject is changed, the processor 120 may control the display 140 so that the indicator 73 for displaying the scannable time includes an indicator for displaying an updated scannable time for at least one diagnostic subject for which the scan has been performed in the past. In this case, updating the information about the remaining scannable time for at least one diagnostic subject for which the scan has been performed in the past before the diagnostic subject is changed may include increasing the remaining scannable time for at least one diagnostic subject for which the scan has been performed in the past during a time at which a scan of the changed diagnostic subject has been performed.

For example, as the scan is performed for 10 seconds after the diagnostic subject is changed to the bladder of the pregnant woman, the processor 120 may modify the indicator 73 for displaying the scannable time to be displayed on the display 140 as illustrated in FIG. 20.

For example, as illustrated in FIG. 20, as the scan for the bladder of the pregnant woman is performed for 10 seconds, the processor 120 may modify the indicator 73 for displaying the scannable time to increase the length of the bar of the second sub-indicator 73*b* displaying the information about the time at which the scan has been performed and decrease the length of the bar of the third sub-indicator 73*c* displaying the information about the remaining scannable time for each object, among the sub-indicators of the indicator 733 for displaying the scannable time for the bladder of the pregnant woman. In addition, the indicator of the character form included in the third sub-indicator 73*c* may also be changed from 1 minutes which is the maximum scannable time, to 50 seconds decreased by the amount of time it took to perform the scan (for example, 10 seconds).

The processor 120 may also modify the indicator 73 for displaying the scannable time to increase the length of the bar of the third sub-indicator 73*c* displaying the information about the remaining scannable time for each object among the sub-indicators of the indicator 732 for displaying the scannable time for the abdomen of the pregnant woman. Accordingly, the processor 120 may display the length of the bar of the second sub-indicator 73*b*, which displays the information about the time at which the scan has been performed among the sub-indicators of the indicator 732 for displaying the scannable time for the abdomen of the pregnant woman, as if it has decreased. In addition, the indicator of the character form included in the third sub-indicator 73*c* may also change the remaining scannable time from 3 minutes and 40 seconds to 3 minutes and 50 seconds increased by an amount of time it took to perform the bladder scan of the pregnant woman (for example, 10 seconds).

Figure 21:
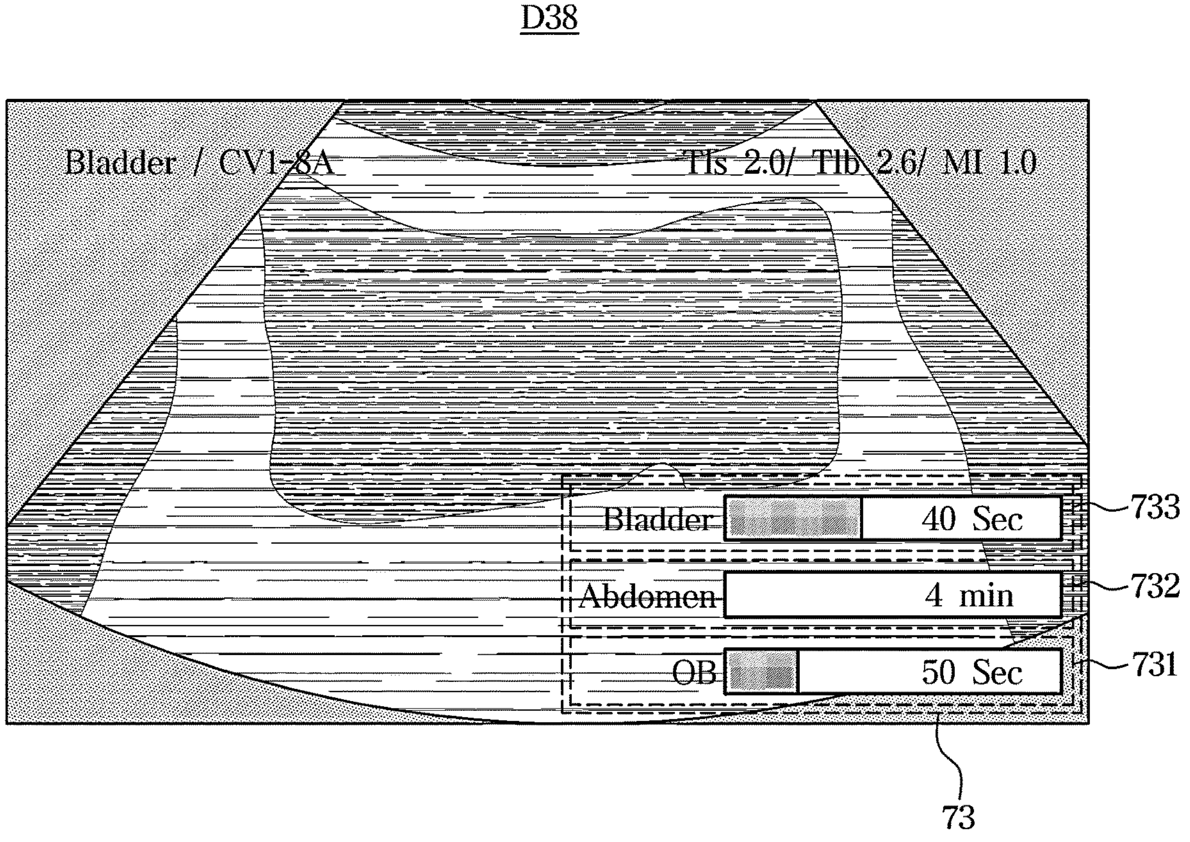
FIG. 21 is a diagram illustrating a screen D38 and a plurality of indicators displayed on the display of the ultrasonic diagnostic device following FIG. 20 according to another embodiment.

FIG. 21 is a diagram illustrating a screen D38 and a plurality of indicators displayed on the display of the ultrasonic diagnostic device following FIG. 20 according to another embodiment.

Figure 22:
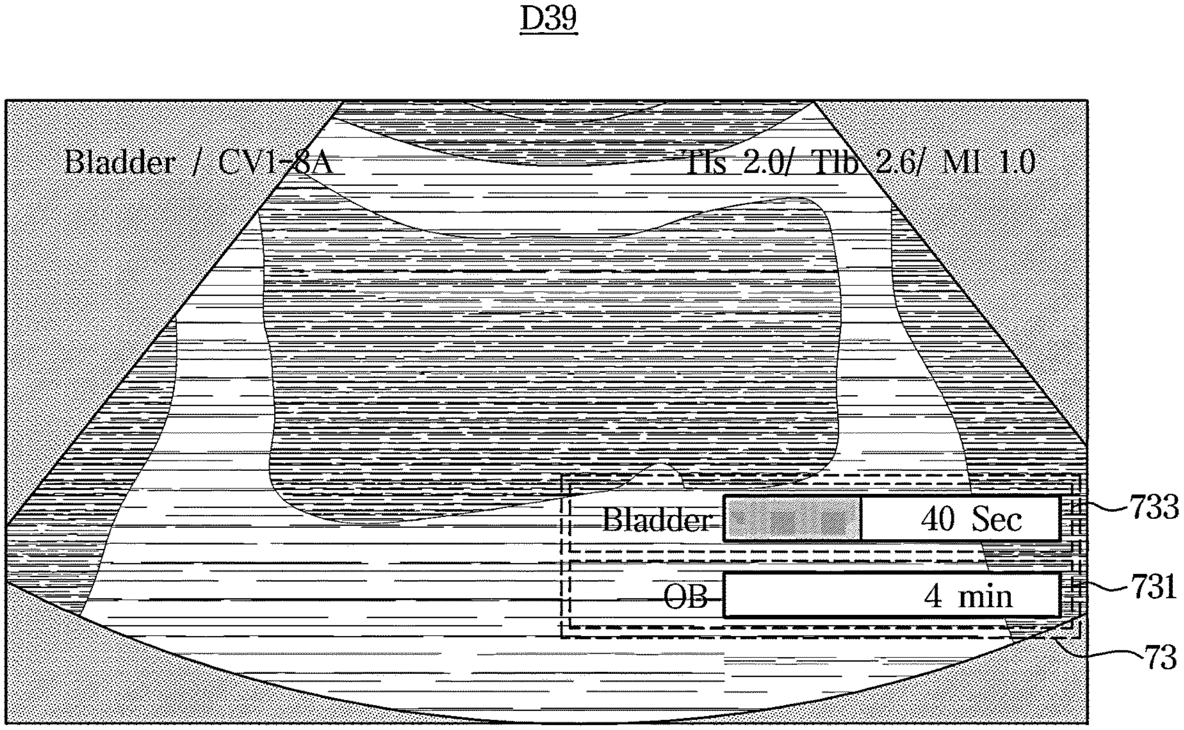
FIG. 22 is a diagram illustrating a screen D39 and a plurality of indicators displayed on the display of the ultrasonic diagnostic device following FIG. 21 according to another embodiment.

FIG. 22 is a diagram illustrating a screen D39 and a plurality of indicators displayed on the display of the ultrasonic diagnostic device following FIG. 21 according to another embodiment.

The processor 120 may modify the indicator 73 for displaying the scannable time based on the scannable time being changed to the maximum scannable time as the scannable time for the object or diagnostic subject is updated in the process in which the scan is performed. That is, as the scan is performed, the processor 120 may control the display 140 so that the indicator 73 for displaying the scannable time includes information that the scannable time is changed to the maximum scannable time.

As described above, as the scan for the changed object or diagnostic subject is performed, the scannable times for the object or diagnostic subject before the change may be updated. Updating the scannable time may include increasing the scannable time for the object or diagnostic subject before the change during a time at which the scan for the changed object or diagnostic subject has been performed. As the scannable time for the object or diagnostic subject before the change increases, the scannable time for the object or diagnostic subject before the change may reach a preset maximum scannable time.

For example, as the scan for the bladder of the pregnant woman is performed for 10 seconds, the remaining scannable time for the abdomen of the pregnant woman may be increased from 3 minutes and 50 seconds to 4 minutes increased by the amount of time it took to perform the bladder scan of the pregnant woman (for example, 10 seconds). That is, the scannable time for the abdomen of the pregnant woman may be changed to 4 minutes, which is the maximum scannable time.

Accordingly, as illustrated in FIG. 21, the processor 120 may not display the bar of the second sub-indicator 73*b*, which displays the information about the time at which the scan has been performed, among the sub-indicators of the indicator 732 for displaying the scannable time for the abdomen of the pregnant woman, and may display the bar of the third sub-indicator 73*c* displaying the information about the remaining scannable time, with a length corresponding to the maximum scannable time. In addition, the processor 120 may also change the remaining scannable time for the indicator of the character form included in the third sub-indicator 73*c* to 4 minutes which is the maximum scannable time.

The processor 120 may also not display an indicator for displaying the scannable time for each object or diagnostic subject based on the scannable time for each object or diagnostic subject being changed to the maximum scannable time.

For example, as illustrated in FIG. 22, the processor 120 may not display the indicator 732 for displaying the scannable time for the abdomen of the pregnant woman based on the scannable time for the abdomen of the pregnant woman being changed to the maximum scannable time for the abdomen of the pregnant woman.

Figure 23:
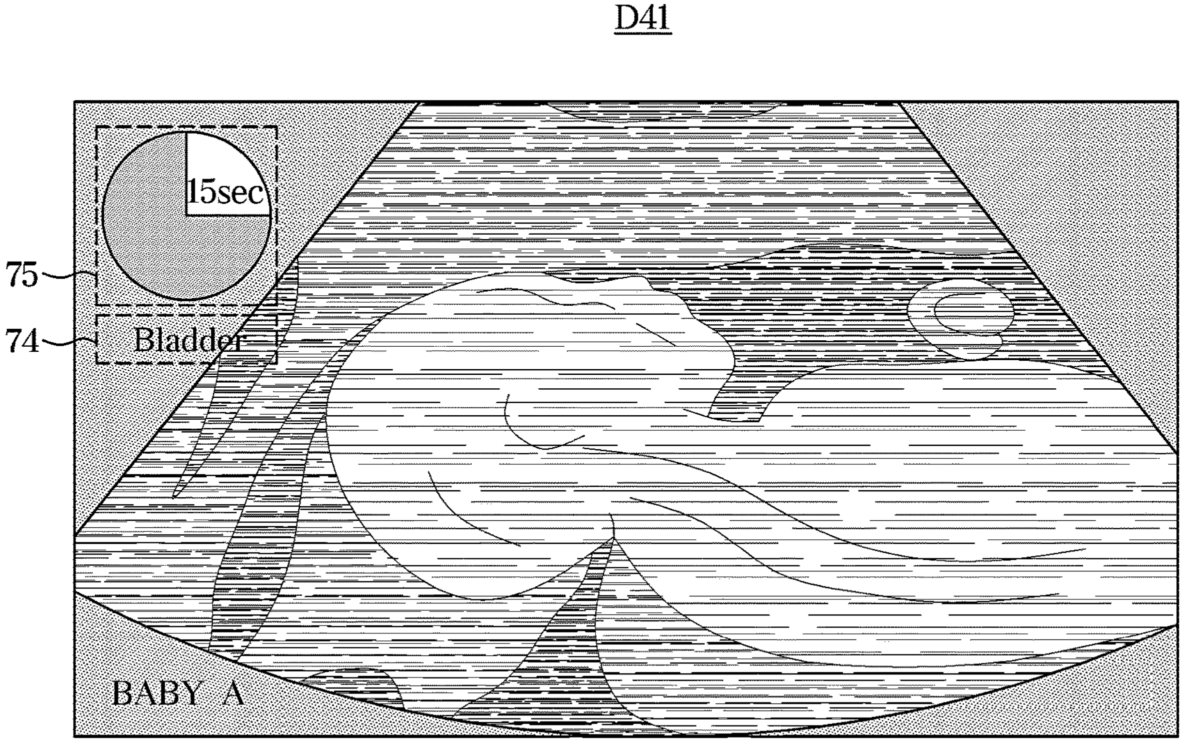
FIG. 23 is a diagram illustrating a screen D41 and a form of an indicator for displaying a scannable time displayed on the display of the ultrasonic diagnostic device according to an embodiment.

FIG. 23 is a diagram illustrating a screen D41 and a form of an indicator for displaying a scannable time displayed on the display of the ultrasonic diagnostic device according to an embodiment.

Figure 24:
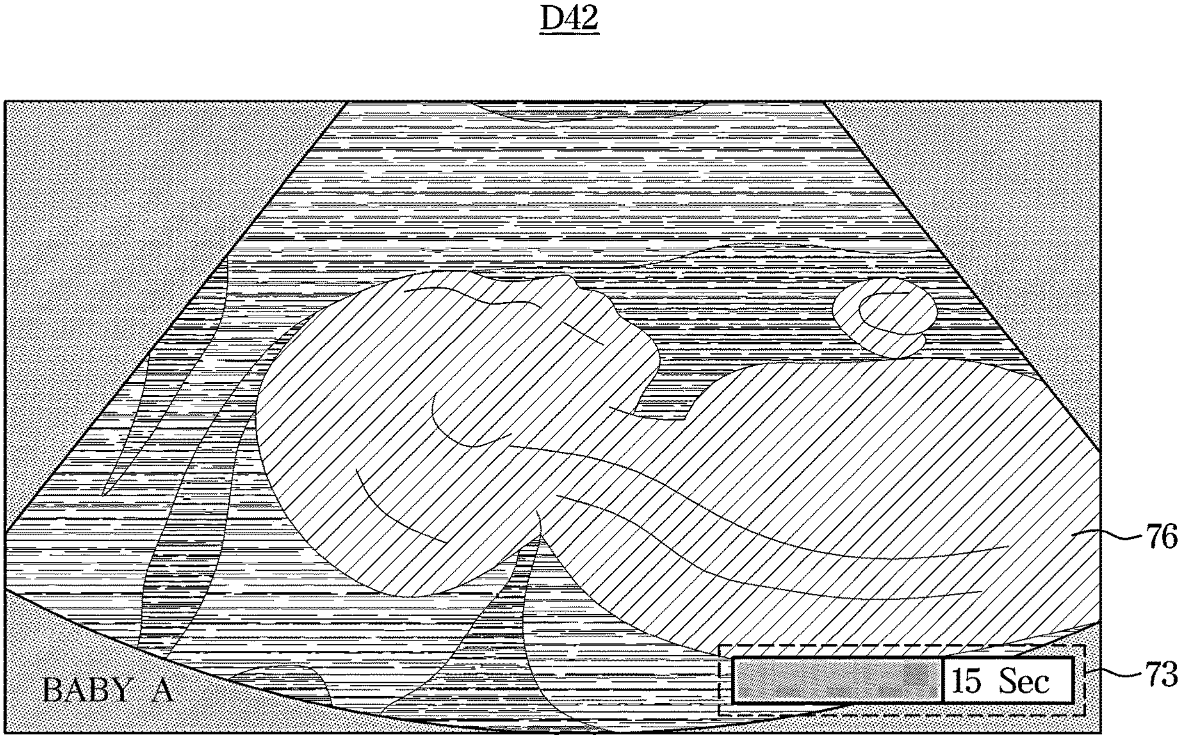
FIG. 24 is a diagram illustrating a screen D42 and a form of an indicator for displaying a scannable time displayed on the display of the ultrasonic diagnostic device according to an embodiment.

FIG. 24 is a diagram illustrating a screen D42 and a form of an indicator for displaying a scannable time displayed on the display of the ultrasonic diagnostic device according to an embodiment.

According to various embodiments, the processor 120 may control the display 140 so that the indicator 73 for displaying the scannable time displays the scannable time for the object or diagnostic subject currently being scanned.

For example, when the scan object is changed to the fetus while the scan for the abdomen of the pregnant woman is performed, the processor 120 may control the display 140 so that the indicator 73 for displaying the scan time includes only the indicator for displaying the scannable time for the fetus and does not include the indicator for displaying the scannable time for the abdomen of the pregnant woman on which an examination is performed before scanning the fetus.

According to various embodiments, the processor 120 may control the display 140 so that the indicator 73 for displaying the scannable time displays the scannable time for the object or diagnostic subject that has been scanned in the past, excluding the object or diagnostic subject that is currently being scanned.

For example, when the scan object is changed to the fetus while the scan for the abdomen of the pregnant woman is performed, the processor 120 may control the display 140 so that the indicator 73 for displaying the scan time includes only the indicator for displaying the scannable time for the abdomen of the pregnant woman and does not include the indicator for displaying the scannable time for the fetus.

According to various embodiments, the processor 120 may control the display 140 so that the indicator 73 for displaying the scannable time displays the scannable time for the object or diagnostic subject that has been scanned in the past as well as the object or diagnostic subject that is currently being scanned.

For example, when the scan object is changed to the fetus while the scan for the abdomen of the pregnant woman is performed, the processor 120 may control the display 140 so that the indicator 73 for displaying the scan time includes the indicator for displaying the scannable time for the fetus as well as the indicator for displaying the scannable time for the abdomen of the pregnant woman.

According to various embodiments, the indicator 73 for displaying the scannable time may be implemented in various types and forms.

As described above, the indicator may display the information about the scannable time in the form of a bar, but may also display the scannable time for each object using a character 74 and a circular shape 75 as illustrated in FIG. 23.

The implementation form and/or location of the indicator 73 displaying the information about the scannable time is not limited to this disclosure, and any form and/or location capable of efficiently delivering the information about the scannable time to the user may be adopted.

According to various embodiments, when the maximum scannable time for each object or diagnostic subject is exceeded, the processor 120 may display that the maximum scannable time has been exceeded in various types and manners.

For example, processor 120 may control the display 140 to display a pop-up window, or control an audio to provide a sound notification. Any method capable of effectively notifying the user that the maximum scannable time has been exceeded may be adopted.

For example, the processor 120 may display that the maximum scannable time has been exceeded in a manner capable of delivering to only the user of the ultrasonic diagnostic device 40 that the maximum scannable time has been exceeded and capable of not delivering to a patient that the maximum scannable time has been exceeded.

As another example, the processor 120 may display that the maximum scannable time has been exceeded in a manner capable of delivering to both the user and the patient, rather than only to the user of the ultrasonic diagnostic device 40.

According to various embodiments, the processor 120 may control the probe 20 to not transmit ultrasound from the probe 20 based on the scan time being reached the maximum scannable time. Accordingly, ultrasound energy may not be delivered to the patient.

According to various embodiments, the processor 120 may display that the maximum scannable time is approaching based on the scan time remaining a preset amount of time from the maximum scannable time.

For example, referring to FIG. 24, the processor 120 may display that the maximum scannable time is approaching by causing an area corresponding to the object currently being scanned to flicker red 76 based on the scan time remaining the preset amount of time (for example, 15 seconds) from the maximum scannable time.

Accordingly, the user can intuitively recognize that the maximum scannable time is approaching and use the ultrasonic diagnostic device 40 while complying with the maximum scan time.

Figure 25:
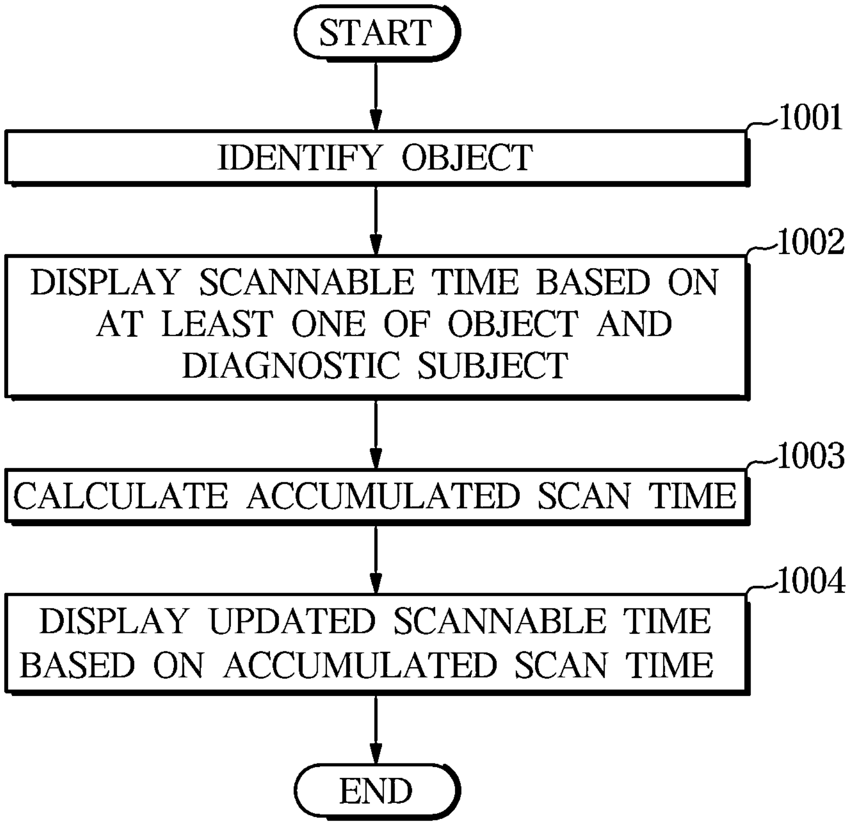
FIG. 25 is an example of a control flow diagram of the ultrasonic diagnostic device 40 according to an embodiment.

FIG. 25 is an example of a control flow diagram of the ultrasonic diagnostic device 40 according to an embodiment.

According to an embodiment, the processor 120 may identify the object included in the scan area (1001). For example, the processor 120 may identify the object using the machine learning model. In this case, the method of identifying the object using the machine learning model may correspond to the method described above with reference to FIGS. 14 and 15.

The processor 120 may display the scannable time determined based on at least one of the identified object or diagnostic subject corresponding thereto (1002). That is, the processor 120 may display the indicator for displaying the scannable time on the display 140 based on at least one of the identified object or diagnostic subject corresponding thereto.

The processor 120 may determine the diagnostic subject for scanning the object based on the object included in the scan area. The diagnostic subject for scanning the identified object may be preset and stored in the memory 150. That is, the processor 120 may determine the diagnostic subject based on the object identified in the ultrasonic image.

The diagnostic subject may be changed by the user before or during the scan. That is, the processor 120 may determine the diagnostic subject for scanning the identified object based on at least one of the user inputs for the identified object or diagnostic subject.

The processor 120 may display, on the display 140, the information about the maximum scan time determined based on the preset basic index as the diagnostic subject is determined. That is, because the scan for the object has not yet been performed, the processor 120 may control the display 140 so that the third sub-indicator 73*c*, which displays the information about the remaining scannable time for the object, indicates the determined maximum scannable time. In this case, the second sub-indicator 73*b*, which displays the information about the time at which the scan has been performed, may not be displayed. For example, when the identified object is the abdomen of the pregnant woman, the preset maximum scannable time may be 4 minutes, and accordingly, the processor 120 may control the display 140 so that the third sub-indicator 73*c* may display 4 minutes.

The processor 120 may calculate the accumulated scan time as the scan is performed (1003). In this case, the accumulated scan time may correspond to the time added up not only the scan time when the scan for a given object or diagnostic subject has been performed continuously, but also the scan time when the scan has been performed discontinuously. For example, when the abdomen of the pregnant woman is scanned for 10 seconds, the bladder of the pregnant woman is scanned for 20 seconds, and the abdomen of the pregnant woman is scanned again for 10 seconds, the accumulated scan time as the scan is performed may be 10 seconds+10 seconds=20 seconds.

The processor 120 may control the display 140 to display an updated scannable time based on the calculated cumulative scan time (1004).

Specifically, the processor 120 may modify the indicator 73 for displaying the scan time displayed on the display 140 at step 1002 by reflecting the accumulated scan time. For example, as the abdomen of the pregnant woman is scanned for 10 seconds, the bladder of the pregnant woman is scanned for 20 seconds, and the abdomen of the pregnant woman is scanned again for 10 seconds, because the maximum scannable time for the abdomen of the pregnant woman is 4 minutes when the accumulated scan time for the abdomen of the pregnant woman is 20 seconds, the processor 120 may modify the indicator 73 for displaying the scan time displayed so that the third sub-indicator 73*c* may indicate 3 minutes and 40 seconds. That is, the processor 120 may modify the indicator 73 for displaying the scan time displayed so that the length of the bar of the second sub-indicator 73*b* increases by a length corresponding to 20 seconds out of the total 4 minutes and the length of the bar of the third sub-indicator 73*c* decreases by a length corresponding to 3 minutes and 40 seconds out of the total 4 minutes.

Figure 26:
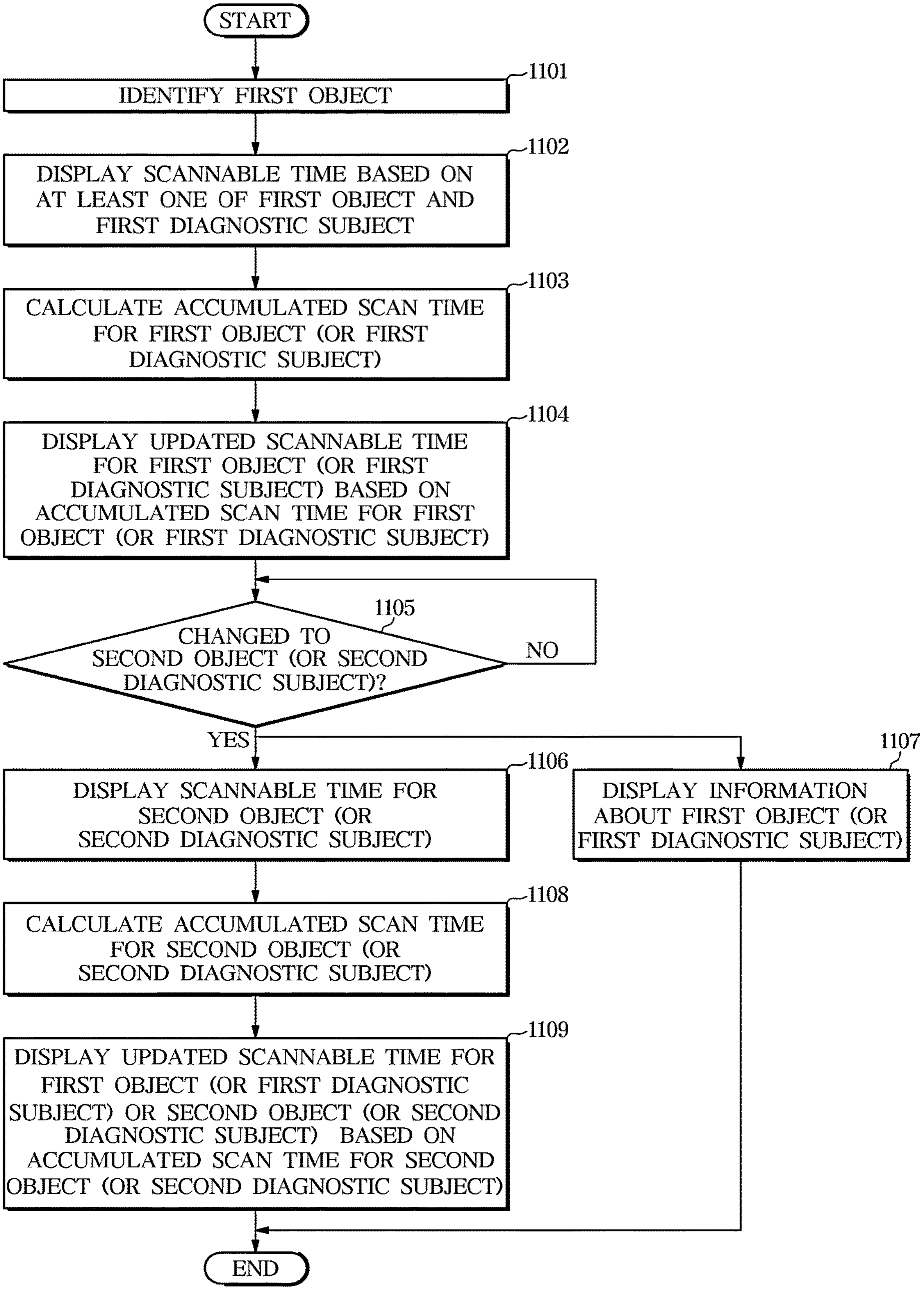
FIG. 26 is another example of a control flow diagram of the ultrasonic diagnostic device 40 according to an embodiment.

FIG. 26 is another example of a control flow diagram of the ultrasonic diagnostic device 40 according to an embodiment.

Steps 1101 to 1104 of FIG. 26 may correspond to steps 1001 to 1004 described above in FIG. 25.

The processor 120 may determine whether the diagnostic subject has been changed from a first object (or a first diagnostic subject) to a second object (or a second diagnostic subject) (1105). In this case, identifying the object in the ultrasonic image corresponding to the current scan area and determining whether at least one of the diagnostic subject and the object has changed may be performed by the machine learning model. A method of determining whether at least one of the diagnostic subject and the object has been changed using the machine learning model may correspond to the method described above with reference to FIGS. 14 and 15.

When it is determined that the diagnostic subject has been changed from the first object (or the first diagnostic subject) to the second object (or the second diagnostic subject) (YES in 1105), the processor 120 may display a scannable time for the second object (or the second diagnostic subject) (1106). That is, the processor 120 may display an indicator for displaying the scannable time for the second object (or the second diagnostic subject) on the display 140.

In this case, the processor 120 may display information about the first object (or the first diagnostic subject) before the change, together with the indicator for displaying the scannable time for the second object (or the second diagnostic subject) (1107). The information about the first object (or the first diagnostic subject) may include a scannable time for the first object (or the first diagnostic subject), and the processor 120 may display an indicator for displaying the scannable time for the first object (or the first diagnostic subject) before the change, together with the indicator for displaying the scannable time for the second object (or the second diagnostic subject).

The processor 120 may calculate the accumulated scan time based on the scan for the second object (or the second diagnostic subject) (1108). In this case, the accumulated scan time may correspond to the time added up not only the scan time when the scan for a given object or diagnostic subject has been performed continuously, but also the scan time when the scan has been performed discontinuously. For example, when the abdomen of the pregnant woman is scanned for 10 seconds, the bladder of the pregnant woman is scanned for 20 seconds, and the abdomen of the pregnant woman is scanned again for 10 seconds, the accumulated scan time as the scan is performed may be 10 seconds+10 seconds=20 seconds.

The processor 120 may control the display 140 to display an updated scannable time for the first object (or the first diagnostic subject) and/or the second object (or the second diagnostic subject) based on the calculated cumulative scan time (1109). That is, the processor 120 may modify the indicator 73 for displaying the scan time to be displayed on the display 140 at steps 1106 and 1107 by reflecting the accumulated scan time.

For example, a case in which the first object is the fetus and the changed second object is the abdomen of the pregnant woman, and the fetus is scanned for 40 seconds and the abdomen of the pregnant woman is scanned for 20 seconds will be described below.

The processor 120 may modify the indicator 73 for displaying the scan time displayed so that the second sub-indicator 73*b* may indicate 20 seconds and the third sub-indicator 73*c* may indicate 3 minutes and 40 seconds based on the maximum scannable time for the abdomen of the pregnant woman being 4 minutes and the abdomen of the pregnant woman being scanned for 20 seconds. That is, the processor 120 may modify the indicator 73 for displaying the scan time displayed so that the length of the bar of the second sub-indicator 73*b* increases by the length corresponding to 20 seconds out of the total 4 minutes and the length of the bar of the third sub-indicator 73*c* decreases by the length corresponding to 3 minutes and 40 seconds out of the total 4 minutes. Accordingly, the processor 120 may display an updated scannable time for the second object by reflecting the accumulated scan time calculated as the scan for the second object is performed.

Because the maximum scannable time for the fetus is 1 minute and the fetus has been scanned for 30 seconds before the abdomen of the pregnant woman has been scanned for 20 seconds, at a time point where the object is changed to the abdomen of the pregnant woman, the scannable time for the fetus may correspond to 30 seconds. Therefore, at the time point where the object is changed to the abdomen of the pregnant woman, the second sub-indicator 73*b* may indicate 40 seconds and the third sub-indicator 73*c* may indicate 20 seconds.

In this case, the processor 120 may modify the indicator 73 for displaying the scan time so that the second sub-indicator 73*b* may indicate 20 seconds and the third sub-indicator 73*c* may indicate 40 seconds based on the scan being performed on the abdomen of the pregnant woman for 20 seconds. That is, the processor 120 may modify the indicator 73 for displaying the scan time displayed so that the length of the bar of the second sub-indicator 73*b* decreases by the length corresponding to 20 seconds out of the total 1 minutes and the length of the bar of the third sub-indicator 73*c* increases by a length corresponding to 40 seconds out of the total 1 minute. Accordingly, the processor 120 may display an updated scannable time for the first object by reflecting the accumulated scan time calculated as the scan for the second object is performed.

As is apparent from the above, according to an aspect of the disclosure, an ultrasonic device can be used safely by guiding a user to an appropriate scan time.

According to an aspect of the disclosure, safety in especially obstetric examinations can be improved by distinguishing and guiding an accumulated scan time for each diagnostic subject or object.

According to an aspect of the disclosure, the safety of the use of ultrasonic diagnostic devices can be ensured even when the use of the ultrasonic diagnostic devices by non-professionals increases in the future.

However, effects that may be achieved by the ultrasonic diagnostic device and the control method thereof of this disclosure are not limited to the effects mentioned above, and other effects not mentioned may be clearly understood by those skilled in the art to which the disclosure belongs from the above description. The disclosed embodiments may be implemented in the form of a recording medium storing instructions executable by a computer. The instructions may be stored in the form of program code, and when executed by a processor, a program module may be created to perform the operations of the disclosed embodiments. The recording medium may be implemented as a computer-readable recording medium.

A computer-readable recording medium includes any type of recording medium in which instructions readable by the computer are stored. For example, the recording medium may include a read only memory (ROM), a random access memory (RAM), a magnetic tape, a magnetic disk, a flash memory, an optical data storage device, and the like.

The computer-readable recording medium may be provided in the form of a non-transitory storage medium. Herein, the 'non-transitory storage medium' simply means that it is a tangible device and does not contain signals (e.g. electromagnetic waves), and this term does not distinguish between a case where data is semi-permanently stored in a storage medium and a case where data is stored temporarily. For example, the 'non-transitory storage medium' may include a buffer where data is temporarily stored.

According to an embodiment, the methods according to various embodiments disclosed in this document may be included and provided in a computer program product. The computer program product is a commodity and may be traded between sellers and buyers. The computer program product may be distributed in the form of a machine-readable recording medium (e.g., compact disc read only memory (CD-ROM)), or may be distributed (e.g., downloaded or uploaded) online, through an application store (e.g., Play Store™) or directly between two user devices (e.g., smartphones). In the case of online distribution, at least a portion of the computer program product (e.g., a downloadable app) may be at least temporarily stored or created temporarily in the machine-readable recording medium, such as the memory of a manufacturer server, an application store server, and a relay server.

The foregoing has illustrated and described the specific embodiments. However, it should be understood by those of skilled in the art that the disclosure is not limited to the above-described embodiments, and various changes and modifications may be made without departing from the technical idea of the disclosure described in the following claims.

What is claimed is:

1. A control method of an ultrasonic diagnostic device, which comprises a display configured to display an ultrasonic image corresponding to a scan area scanned by a probe, including:

identifying an object included in the scan area;

determining a diagnostic subject based on at least one of the object or a user input received from an input interface;

determining a scannable time for each object or diagnostic subject; and displaying an indicator for displaying the scannable time on the display, wherein the displaying of the indicator for displaying the scannable time on the display includes:

displaying a first sub-indicator displaying information about the object or the diagnostic subject;

displaying a second sub-indicator displaying information about a time at which a scan for the object or the diagnostic subject has been performed; and displaying a third sub-indicator displaying information about a remaining scannable time for the object or the diagnostic subject, and wherein the combination of the second sub-indicator and the third sub-indicator displays the maximum scannable time for each object or diagnostic subject.

2. The control method according to claim 1, wherein the displaying of the indicator for displaying the scannable time on the display includes displaying an indicator for displaying a scannable time for a changed object or a changed diagnostic subject based on the object or the diagnostic subject is changed.

3. The control method according to claim 2, wherein the displaying of the indicator for displaying the scannable time on the display includes displaying an indicator for displaying a scannable time for the object before the change or the diagnostic subject before the change based on the object or the diagnostic subject is changed.

4. The control method according to claim 3, further includes calculating an accumulated scan time for the changed object or the changed diagnostic subject based on a scanning for the changed object or the changed diagnostic subject is performed.

5. The control method according to claim 4, wherein the displaying of the indicator for displaying the scannable time on the display includes updating and displaying the scannable time for the changed object or the changed diagnostic subject based on the calculated cumulative scan time.

6. The control method according to claim 5, wherein the updating and displaying of the scannable time for the changed object or the changed diagnostic subject based on the calculated cumulative scan time includes increasing a ratio of the second sub-indicator and decreasing a ratio of the third sub-indicator, in the indicator for displaying the scannable time by a ratio of the calculated cumulative scan time to the maximum scannable time.

7. The control method according to claim 4, wherein the displaying of the indicator for displaying the scannable time on the display includes updating and displaying the scannable time for the object before change or the diagnostic subject before change based on the calculated cumulative scan time.

8. The control method according to claim 7, wherein the updating and displaying of the scannable time for the object before change or the diagnostic subject before change based on the calculated cumulative scan time comprises decreasing a ratio of the second sub-indicator and increasing a ratio of the third sub-indicator, in the indicator for displaying the scannable time by a ratio of the calculated cumulative scan time to the maximum scannable time.

9. The control method according to claim 1, wherein the identifying of the object included in the scan area includes being performed by a machine learning model stored in a memory.

10. An ultrasonic diagnostic device comprising:

a display configured to display an ultrasonic image;

an input interface configured to receive a user input for controlling display of the ultrasonic image; and a processor configured to:

identify an object included in a scan area, determine a diagnostic subject based on at least one of the user input received from the input interface or the object, determine a scannable time for each object or diagnostic subject, and control the display to display an indicator for displaying the scannable time, wherein the indicator for displaying the scannable time includes at least one of a first sub-indicator displaying information about the object or the diagnostic subject, a second sub-indicator displaying information about a time at which a scan for the object or the diagnostic subject has been performed, and a third sub-indicator displaying information about a remaining scannable time for the object or the diagnostic subject, and wherein the combination of the second sub-indicator and the third sub-indicator displays the maximum scannable time for each object or diagnostic subject.

11. The ultrasonic diagnostic device according to claim 10, wherein the processor configured to display an indicator for displaying a scannable time for a changed object or a changed diagnostic subject based on the object or the diagnostic subject is changed.

12. The ultrasonic diagnostic device according to claim 11, wherein the processor further configured to display an indicator for displaying a scannable time for the object before the change or the diagnostic subject before the change based on the object or the diagnostic subject is changed.

13. The ultrasonic diagnostic device according to claim 12, wherein the processor configured to calculate an accumulated scan time for the changed object or the changed diagnostic subject based on a scanning for the changed object or the changed diagnostic subject is performed.

14. The ultrasonic diagnostic device according to claim 13, wherein the processor configured to update and display the scannable time for the changed object or the changed diagnostic subject based on the calculated cumulative scan time.

15. The ultrasonic diagnostic device according to claim 14, wherein the processor configured to increase a ratio of the second sub-indicator and decreases a ratio of the third sub-indicator, in the indicator for displaying the scannable time by a ratio of the calculated cumulative scan time to the maximum scannable time.

16. The ultrasonic diagnostic device according to claim 13, wherein the processor configured to update and display the scannable time for the object before change or the diagnostic subject before change based on the calculated cumulative scan time.

17. The ultrasonic diagnostic device according to claim 16, wherein the processor configured to decrease a ratio of the second sub-indicator and increases a ratio of the third sub-indicator, in the indicator for displaying the scannable time by a ratio of the calculated cumulative scan time to the maximum scannable time.

18. The ultrasonic diagnostic device according to claim 10, further comprising a memory configured to store a machine learning model, wherein the processor configured to identify the object by the machine learning model.

* * * * *